US009239903B2

(12) United States Patent
Scheler

(10) Patent No.: US 9,239,903 B2
(45) Date of Patent: Jan. 19, 2016

(54) DETERMINATION OF OUTPUT OF BIOCHEMICAL REACTION NETWORKS

(71) Applicant: Gabriele Scheler, Mountain View, CA (US)

(72) Inventor: Gabriele Scheler, Mountain View, CA (US)

( * ) Notice: Subject to any disclaimer, the term of this patent is extended or adjusted under 35 U.S.C. 154(b) by 394 days.

(21) Appl. No.: 13/789,278

(22) Filed: Mar. 7, 2013

(65) Prior Publication Data

US 2013/0246019 A1     Sep. 19, 2013

Related U.S. Application Data

(60) Provisional application No. 61/610,413, filed on Mar. 13, 2012.

(51) Int. Cl.
*G06F 17/50* (2006.01)
*G06F 19/12* (2011.01)

(52) U.S. Cl.
CPC ............ *G06F 19/12* (2013.01); *G06F 17/5009* (2013.01)

(58) Field of Classification Search
USPC ........ 703/2; 700/198, 286; 702/19, 52, 53, 84
See application file for complete search history.

(56) References Cited

U.S. PATENT DOCUMENTS

2003/0032576 A1   2/2003  Schilling
2004/0033975 A1   2/2004  Fu et al.
2006/0223917 A1*  10/2006 Hergenrother et al. ......... 524/80
2011/0054855 A1*  3/2011  Doona et al. ...................... 703/2
2014/0235474 A1*  8/2014  Tang et al. ......................... 506/9

OTHER PUBLICATIONS

Chang, et al., "Modeling of Mitochondria Bioenergetics Using a Composable Chemiosmotic Energy Transduction Rate Law: Theory and Experimental Validation", PLoS ONE, vol. 6, Issue 9, e14820, pp. 1-21, (2011).
Rohwer, et al., "Kinetic modelling of plant metabolic pathways", Journal of Experimental Botany, vol. 63, No. 6, pp. 2275-2292, (2012).
Search Report from PCT/US2013/029692 mailed on Jun. 6, 2013.

* cited by examiner

*Primary Examiner* — Thai Phan
(74) *Attorney, Agent, or Firm* — Foley & Lardner LLP; Antoinette F. Konski; Troy D. Smith

(57) ABSTRACT

Provided are methods and devices for modeling biochemical reaction networks. A look up matrix is generated with a number of concentrations for each of the input molecules of the reaction network, coupled with calculated concentrations of the output molecules. Such a look up matrix, by itself or with further fitting, can then be used to predict the output of the reaction network for a given set of input molecule concentrations and can be used to determine the reaction time required for a reaction to reach equilibrium. Additionally, disease states and effects of pharmacological agents can be mathematically analyzed on the basis of comparing the relevant system matrices.

12 Claims, 10 Drawing Sheets

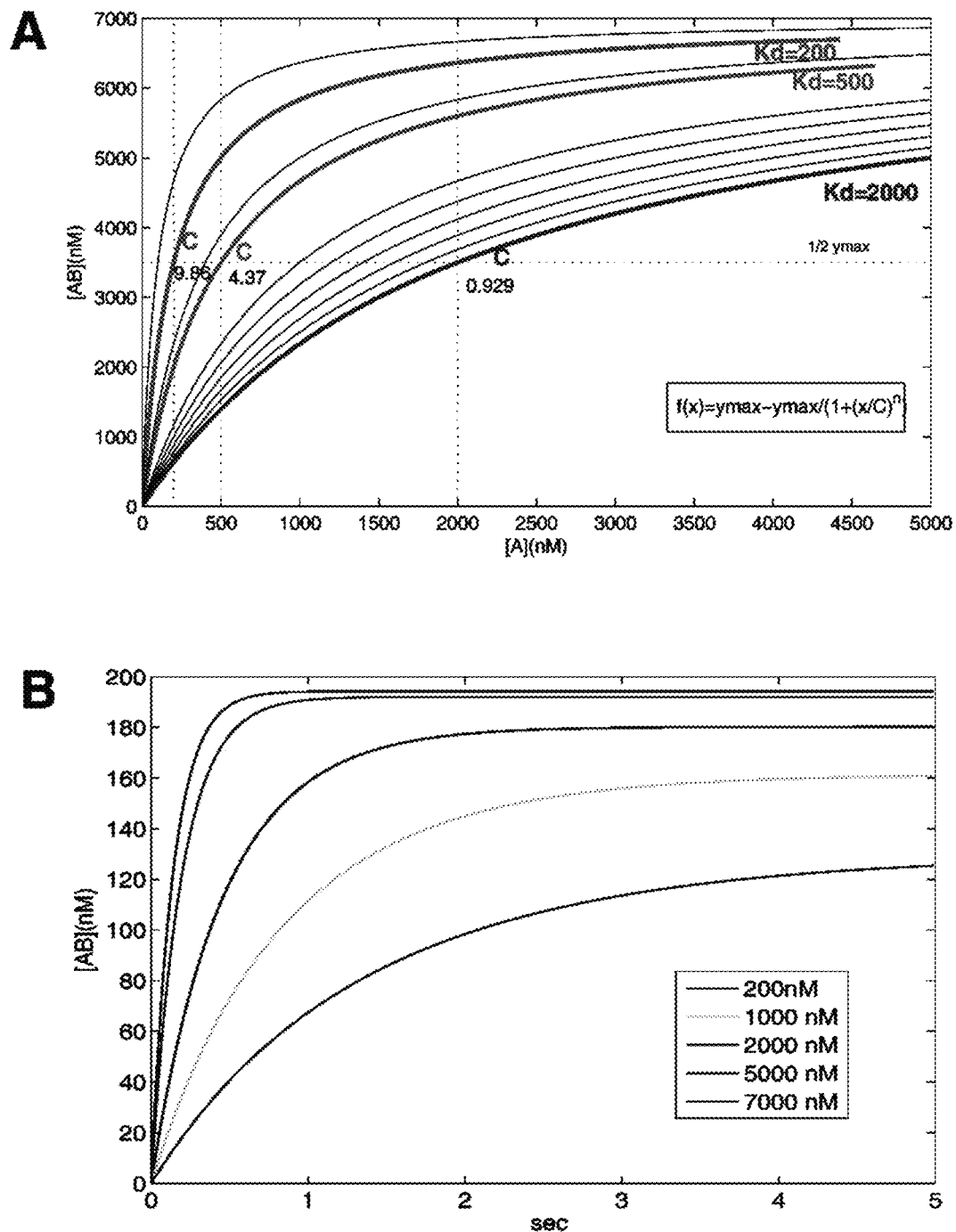
FIG. 1A-B

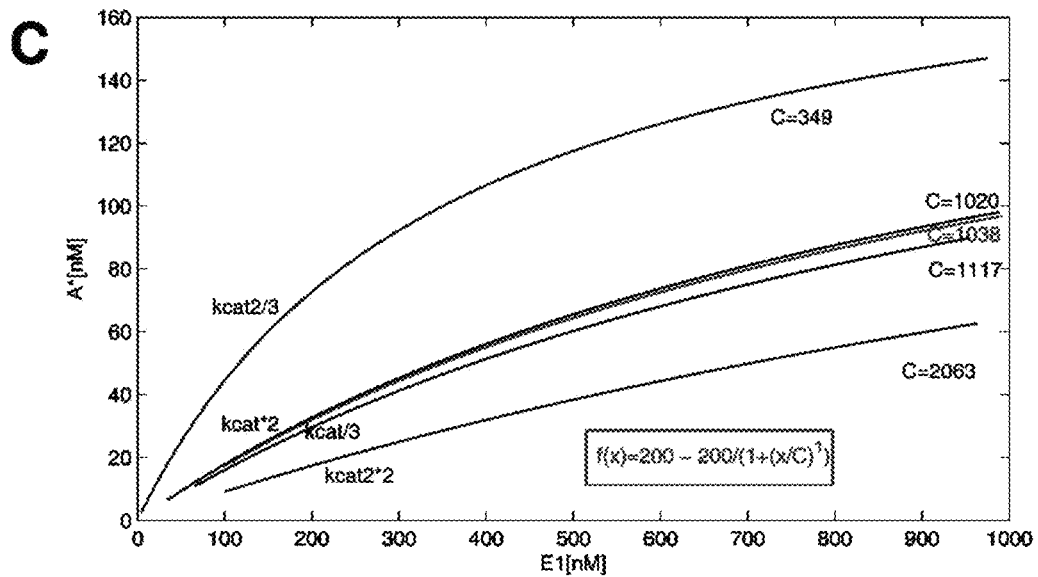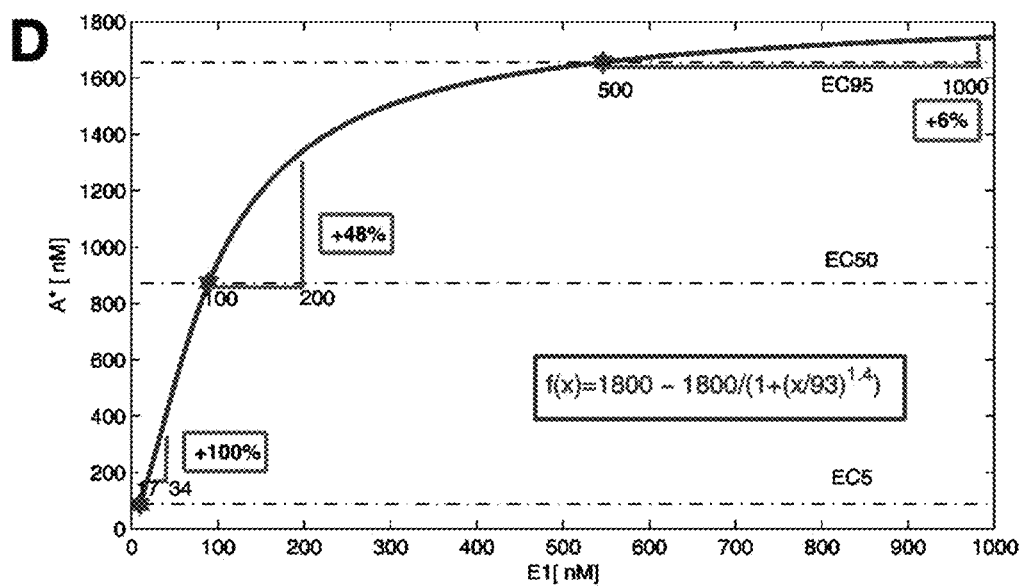
FIG. 1C-D

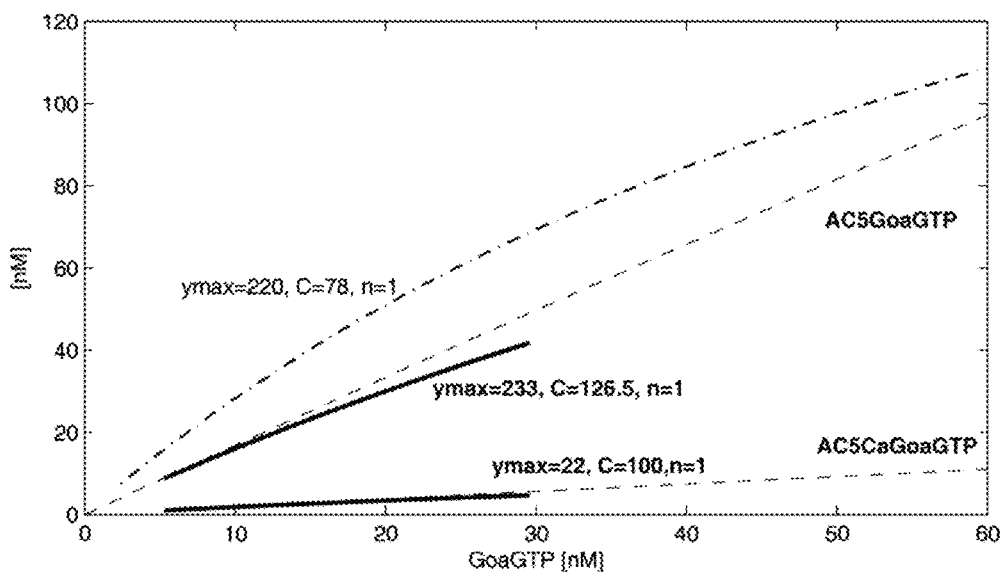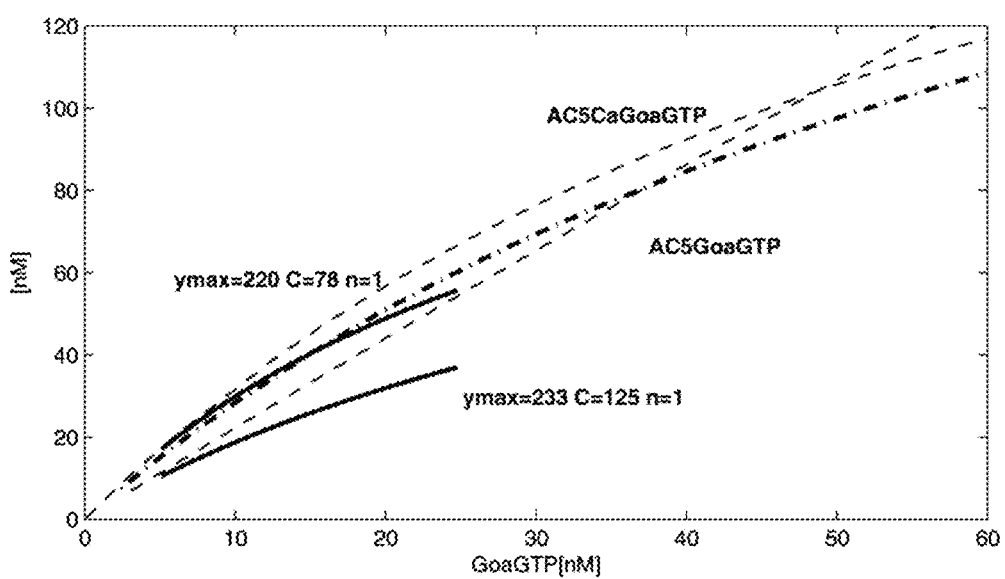
FIG. 3A-B

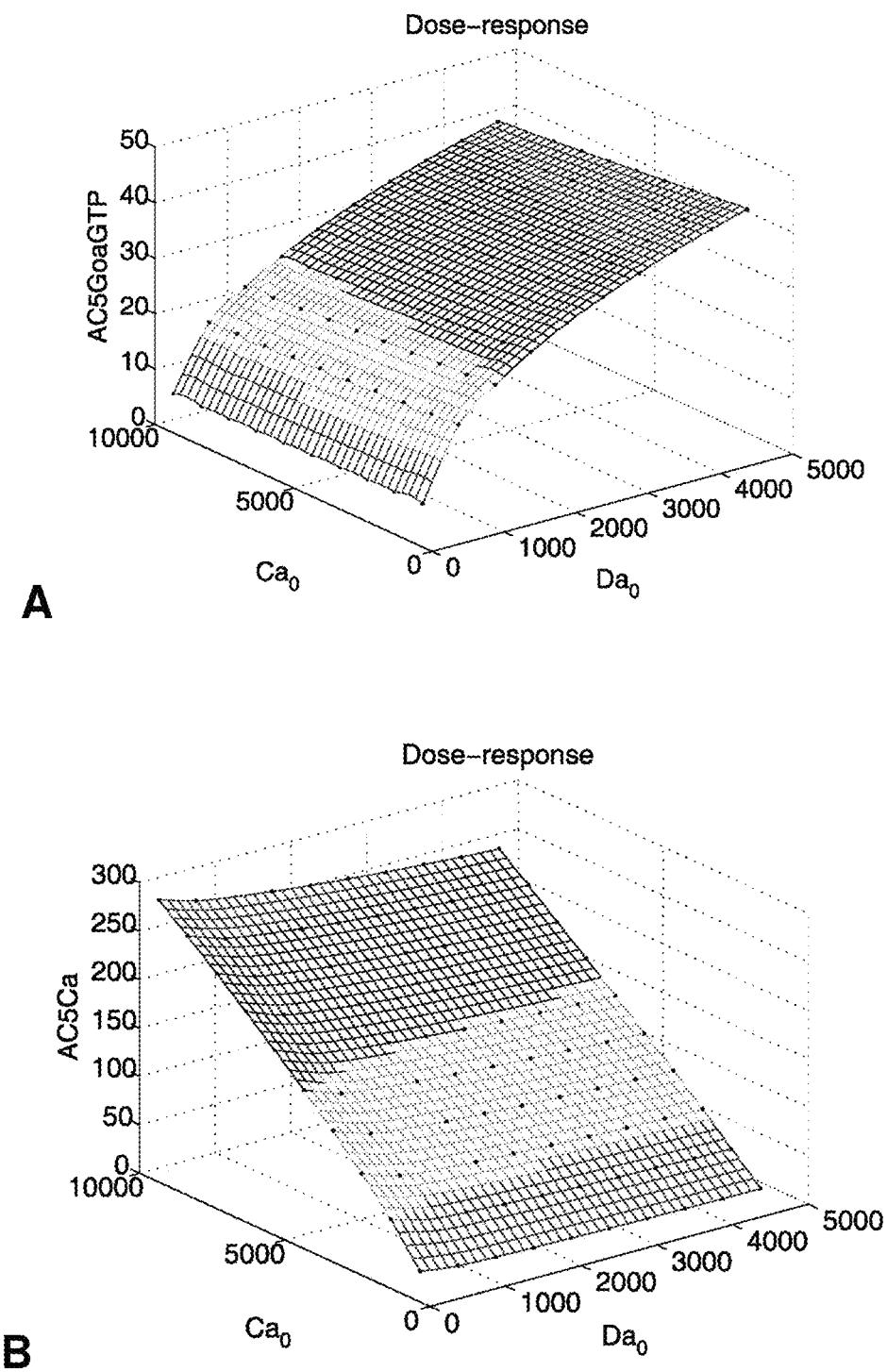
FIG. 4A-B

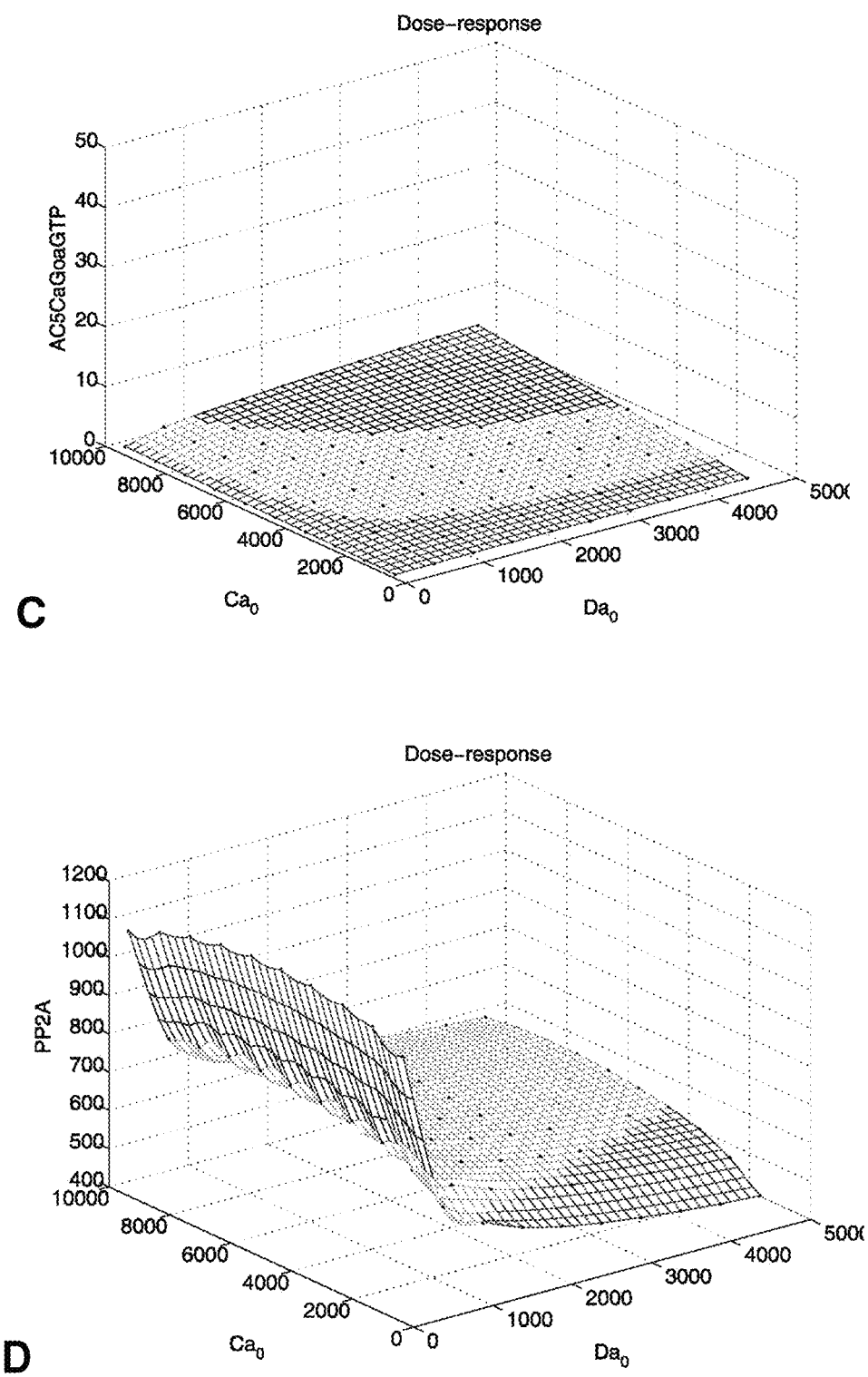
FIG. 4C-D

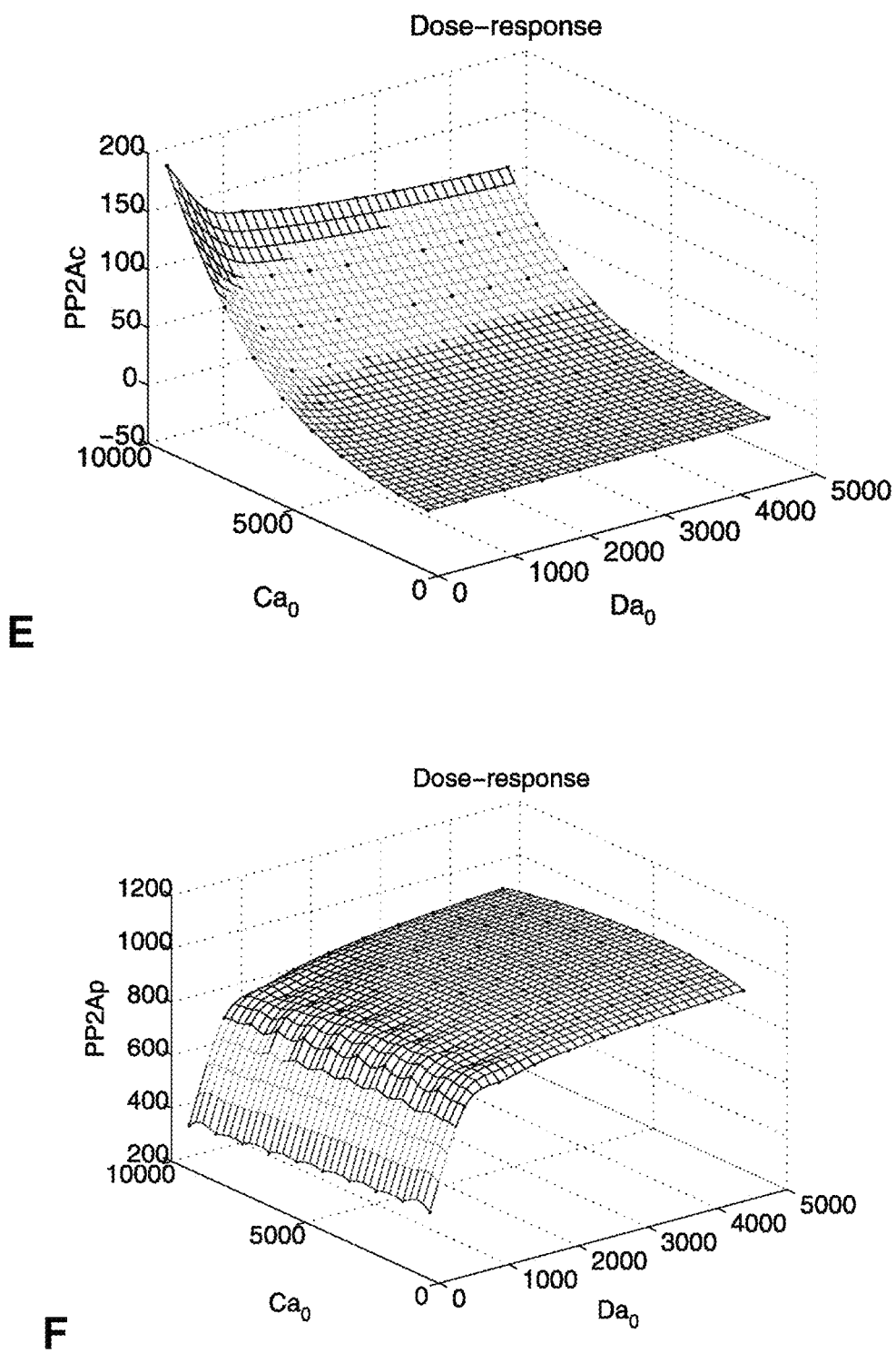
FIG. 4E-F

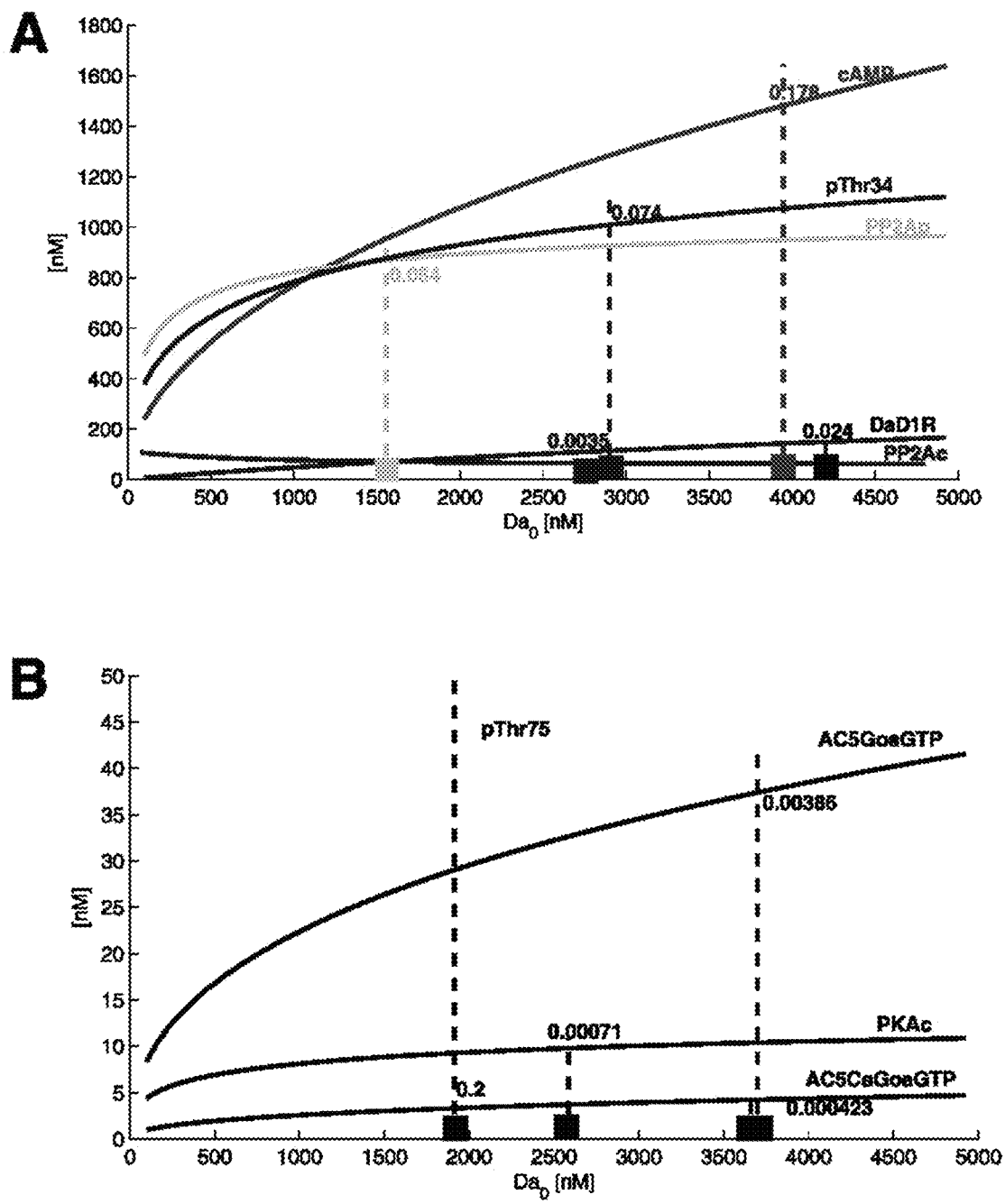
FIG. 6A-B

US 9,239,903 B2

DETERMINATION OF OUTPUT OF BIOCHEMICAL REACTION NETWORKS

CROSS-REFERENCE TO RELATED APPLICATIONS

This application claims the benefit under 35 U.S.C. §119(e) to U.S. Provisional Application Ser. No. 61/610,413, filed Mar. 13, 2012, the contents of which are incorporated by reference in its entirety into the present disclosure.

FIELD OF THE DISCLOSURE

The present invention generally relates to computer aided modeling of biochemical reaction networks, and in particular signal transduction by biochemical reaction networks.

STATE OF THE ART

Biochemical reaction network modeling uses a computer system to simulate certain biochemical reactions based on kinetic rate parameters and concentrations of molecular species. A simulation breaks down metabolic or signaling pathways into their respective reactions and enzymes, and analyzes them within the perspective of the entire network. All reactions are represented by equations, such as the complex formation type (A+B↔AB) or the enzymatic type (S+E↔SE→P+E). In simplified terms, a simulation or reconstruction involves collecting relevant information of a cellular system and then compiling it in a way that makes sense for various types of analyses to be performed.

Biochemical signaling networks are constructed with experimentally obtained constants and analyzed by computational methods to understand their role in complex biological processes. Methods known in the art for modeling a biochemical network include differential equations and stochastic versions thereof, which are embedded in many different simulation tools together with techniques for visualization, parameter fitting to given time-series data, and methods for manipulating the set of elementary reactions of a system.

In performing a dynamic simulation with such a network, for instance, it is necessary to construct an ordinary differential equation (ODE) system that describes the rates of change in each metabolite's concentration or amount. To this end, a rate law, i.e., a kinetic equation, is required for each reaction, and the initial concentrations for the species have to be estimated. Often these rate laws contain kinetic parameters with uncertain values. In many cases it is desired to estimate these parameter values with respect to given time-series data of species concentrations. These methods often result in models with poor generalization properties to new situations, indicating overfitting and lack of robustness in parameter variation. They are therefore of very limited value in guiding research in experimental biology, a deplorable situation well-known to researchers and practitioners in the field.

As exemplified by the dynamic simulation, the standard way to model intracellular signal transduction is by differential equations implementing biochemical reactions using mass-action kinetics. There have been recent developments using stochastic versions of biochemical reactions, for instance on a spatial grid. However, since biochemical reactions, such as protein interactions, proceed in a highly structured cellular environment, with anchoring and scaffolding proteins, cellular organelles, and diffusion in a highly congested environment, stochastic modeling is not adequate to approximate cell-wide interactions. For molecules with intermediate to high expression levels mass-action kinetics on cellular compartments with diffusional interactions are expected to remain the gold standard to solve problems in cellular protein signaling and metabolic interactions.

SUMMARY

The present disclosure provide, in one embodiment, a method for determining the concentrations of one or more output molecules of a biochemical reaction network, which network comprises three or more biochemical reactions that take one or more input molecules as input and the output molecules as output, the method comprising: generating, by a computer, a look up matrix between the output molecules and the input molecules, wherein the matrix comprises a concentration for each of the output molecules produced by the biochemical reaction network from each of the input molecules, at each of one or more concentrations for each of the input molecules, fitting the look up matrix to obtain one or more look up curves, receiving an inquiry comprising an inquiry concentration for each of the input molecules, and determining the concentrations of the output molecules using the look up curves that take the inquiry concentrations as input.

In some embodiments, the fitting comprises fitting each input molecule-output molecule relation in the look up matrix with a saturating hyperbolic function. In some embodiments, the concentrations for each of the input molecules used to generate the look up matrix are taken at after a reaction time required for the biochemical reaction network to have substantially reached an equilibrium. In some embodiments, the method further comprises determining the reaction time.

In some embodiments, the three or more biochemical reactions are reversible. In some embodiments, the method further comprises tuning parameters of one of the look up curves that correspond to one of the biochemical reactions against a target curve, wherein the tuning comprises: (a) adjusting the parameters to fit the curve to the target curve; (b) adjusting the parameters of the curves corresponding to other biochemical reactions that relate to the biochemical reaction according to the adjustment in step (a); (c) determining whether the adjustments in step (b) are within a desired error range; and (d) if the adjustments are not within the desired error range, repeat steps (a)-(c).

In some embodiments, the method further comprises obtaining the target curve in an in vivo or in vitro system that comprises the biochemical reaction network.

Also provided, in one embodiment, is a method for determining the concentrations of one or more output molecules of a biochemical reaction network, which network comprises three or more biochemical reactions that take one or more input molecules as input and the output molecules as output, the method comprising: generating, by a computer, a look up matrix between the output molecules and the input molecules, wherein the matrix comprises a concentration for each of the output molecules produced by the biochemical reaction network from each of the input molecules, at each of one or more concentrations for each of the input molecules, and determining the concentrations of the output molecules by looking up the matrix with inquiry concentrations of the input molecules.

In some embodiments, the three or more biochemical reactions are reversible. In some embodiments, the concentrations of the input and output molecules comprises experimental data or computationally modeled data.

Further provided, in some embodiments, is a computer-implemented method for determining the reaction time required for a biochemical reaction network to have substantially reached an equilibrium, wherein the biochemical reaction network comprises three or more biochemical reactions that take one or more input molecules as input and one or more output molecules as output, the method comprising, (a) generating, by a computer, a look up matrix between the output molecules and the input molecules, wherein the matrix comprises a concentration for each of the output molecules produced by the biochemical reaction network from each of the input molecules, at each of one or more concentrations for each of the input molecules for a time point, and (b) repeat step (a) for a plurality of time points, at least one of the time points of the plurality being likely longer than an estimated maximum reaction time, (c) comparing the concentrations for each of the output molecules at the plurality of time points to determine the reaction time required for the biochemical reaction network to have substantially reached an equilibrium.

In some embodiments, the comparison comprises comparing the difference of concentrations of an output molecule at two time points to a predetermined threshold of concentration change that identifies that an equilibrium is reached.

BRIEF DESCRIPTION OF THE DRAWINGS

Provided embodiments are illustrated by way of example, and not limitation, in the figures of the accompanying drawings in which:

FIG. 1A-D illustrate the properties of protein signaling functions (PSFs). A. Complex formation: PSFs were generated for [A]+[B] ↔ [AB] with Kd=200, 500, 2000, $[A]_0$=10 nM–10 μM; $[B]_0$=7 μM, and fitted with the saturating hyperbolic function shown in the figure. For an elementary reaction, C=Kd. All other curves were generated only by varying C, where $y_{max}$=[B]0 and n=1. The slope at C indicates the signal transmission strength. B. Dynamics of complex formation: [A]+[B] ↔ [AB] with Kd=200, $[B]_0$=200 nM; $[A]_0$=200 nM–7 μM. Increasing concentrations for the source species $[A]_0$ speeds up the reaction. C. Enzymatic Reactions with Reverse Reaction: Example reaction with [A]0=200, $k_{on}$=0.00026; $k_{off}$=1.5; $k_{cat}$=30.4; $k_{cat2}$=0.26 (red, shown as dark gray) and variations (green and blue, shown as light grays). Both the forward reaction ($k_{cat}$) and reverse reaction ($k_{cat2}$) parameters are varied by 30%-200%. Variability in signal transmission is expressed by the fitted parameter C (half-maximal activation) in a uniform way. D. Signal Transmission Strength: A 100% increase of input yields diminishing increases at higher concentrations. Signals are shown at $EC_5$, $EC_{50}$ and $EC_{95}$.

FIG. 3A-B illustrate local adjustment of a transfer function. A. Elementary (dashed) and systemic (continuous) PSFs for two targets of GoaGTP. A new systemic PSF for GoaGTP-AC5CaGoaGTP is defined by functional parameter adjustment (black line). B. Elementary parameters were changed to match the new systemic PSF. For AC5CaGoaGTP, $k_{on}$=0.0192, $k_{off}$=25 was adjusted to $k_{on}$=0.022, $k_{off}$=1.5, for AC5GoaGTP, $k_{on}$=0.0385, $k_{off}$=50 was adjusted to $k_{on}$=0.0495, $k_{off}$=48.5.

FIG. 4A-F show dependence of target species on Ca and Da inputs. The 2D PSF shows species which segregate to only one of the input pathways (A, B, F), a species which remains unresponsive (C), and species which show some signal integration in their input constellation (D, E).

FIG. 6A-B show systemic PSFs for input to target. Shown are $EC_{90}$ and $EC_{10}$ concentrations as cut-off thresholds for effective signaling by input and the slope values at threshold.

Figure 2:
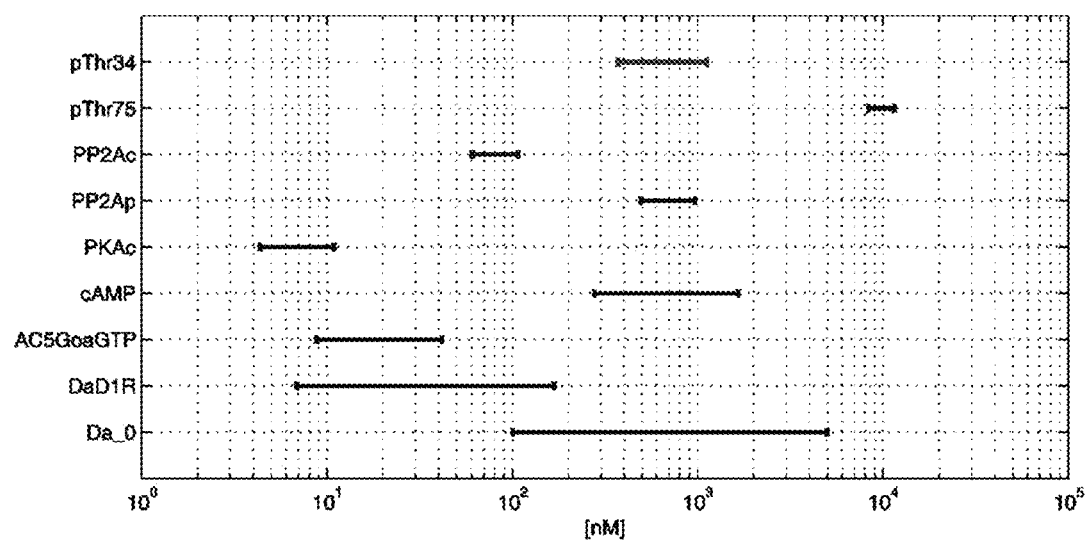
FIG. 2 shows ranges of Concentrations in Response to Input (Da). For a number of relevant target species from the biological model, the range of concentrations for input (Da) from 100 nM to 5 μM is shown (Ca—high, 8 μM).

It will be recognized that some or all of the figures are schematic representations for purposes of illustration and do not necessarily depict the actual relative sizes or locations of the elements shown. The figures are provided for the purpose of illustrating one or more embodiments with the explicit understanding that they will not be used to limit the scope or the meaning of the claims.

DETAILED DESCRIPTION OF THE DISCLOSURE

Throughout this disclosure, various publications, patents and published patent specifications are referenced by an identifying citation. The disclosures of these publications, patents and published patent specifications are hereby incorporated by reference in their entirety into the present disclosure.

As used herein, certain terms have the following defined meanings. Terms that are not defined have their art recognized meanings.

As used in the specification and claims, the singular form "a", "an" and "the" include plural references unless the context clearly dictates otherwise.

As used herein, the term "comprising" is intended to mean that the systems and methods include the recited components or steps, but not excluding others. "Consisting essentially of" when used to define systems and methods, shall mean excluding other components or steps that would materially affect the basic and novel characteristics of the disclosure. "Consisting of" shall mean excluding any step, or component not specified in the claim. Embodiments defined by each of these transition terms are within the scope of this disclosure.

A "processor" is an electronic circuit that can execute computer programs. Examples of processors include, but are not limited to, central processing units, microprocessors, graphics processing units, physics processing units, digital signal processors, network processors, front end processors, coprocessors, data processors and audio processors.

A "memory" refers to an electrical device that stores data for retrieval. In one aspect, a memory is a computer unit that preserves data and assists computation.

A "computer-readable medium," a "storage medium" or "data storage device" refers to a device for recording information. Recording can be done using virtually any form of energy, spanning from manual muscle power in handwriting, to acoustic vibrations in phonographic recording, to electromagnetic energy modulating magnetic tape and optical discs. In one aspect, a storage medium is a computer hard drive. In another aspect, a storage medium is a computer memory. In yet another aspect, a storage medium is a flash drive for a portable or wireless computing device.

A "biochemical reaction network", or simply a "biochemical network" as used herein, refers to a set of metabolic and physical processes in combination which takes one or more molecules as input and produces one or more molecules as output. A biochemical reaction network does not need to encompass all biochemical reactions in a cell. On the other hand, a biochemical reaction network can also include biochemical reactions that may not take place in a cell under natural conditions and only occur when, for instance, an exogenous molecule is introduced into the cell.

Details of the Disclosure

The disclosure provides methods, systems and program codes for modeling of biochemical reaction networks, and in particular determination of the output or input-output relations of the biochemical reaction networks.

As provided, the current methods for biochemical reaction network modeling often result in models with poor generalization properties to new situations, indicating overfitting and lack of robustness in parameter variation. They are therefore of very limited value in guiding research in experimental biology, a deplorable situation well-known to researchers and practitioners in the field. To simplify analysis, it is therefore desirable to separate the computation of reaction time for a species from the computation of the concentration for the species at a given time.

The present inventor has observed that most species in biological signaling networks and similar reaction networks reach fixed equilibria, since systems in practical use are mostly mass conserving, or can be made to be mass conserving by adding a few equations. If an equilibrium point for a species has been reached, the concentration remains unaltered for all time points after the reaction time. Therefore equilibria values are useful in dynamical systems with sufficiently slow dynamics. This eliminates the need to model dynamical systems purely based on rate changes.

Furthermore, experimental dose-response curves directly provide data on input-output species concentrations for given reaction times, including equilibria values when the reactions reach the equilibria.

The present disclosure provides a method of first separate computation of reaction times and concentrations values, and then combining them in a dynamical system. Therefore this system can be independently tuned for both time-series and dose-response data. The computed equilibria values, when matched to experimental dose-response data, provide limiting constraints on possible values of a time-dependent, dynamical system. Therefore great benefits of this technology can be achieved in the goal to match computational models to real experimental results with predictive value.

In this context, the present inventor discovered, unexpectedly and contrary to the conventional wisdom, that calculating the output and the internal states of a biochemical reaction network does not need to be carried out by dynamically modeling the biochemical reaction network with, e.g., differential equations, for specific inputs each time. Instead, all possible inputs can be sampled, and for each sampled input value, necessary computations can be performed to generate a static look up matrix, for a given time point, that correlates the output of the biochemical reaction network with the input. This method is efficient, because the underlying functions are smooth, i.e., sampling is effective with few input concentration sampling points for large input concentration ranges. More specifically, for a biochemical reaction network having multiple input molecules and multiple output molecules, the matrix contains a calculated concentration for each of the output molecules for a number of sets of concentrations of the input molecules.

Therefore, when the concentrations of the output molecules of the biochemical reaction network need to be determined based on a given set of concentrations of the input molecules, the determination can be simply made by looking up the matrix. When the concentrations for each of the input molecules cover a reasonably large physiological range, such a matrix then can be used to determine the output under any physiological conditions.

In another embodiment, moreover, the matrix can be fitted, either altogether or for each input molecule alone, for each biochemical reaction alone, or for each output molecule alone. The fitted functions, in this context, can provide an even greater coverage of all concentrations within the ranges, without being limited to the tested concentration points.

Once the matrix is fitted, the fitting parameters can then be used to represent the fitted matrix. Accordingly, instead of, or in addition to, using the matrix to make the determination, the parameters, which can be stored in a computer-readable medium, can also be used to make the determination.

In some embodiments, the time point at which the matrix is generated is one at or after which the biochemical reactions have substantially reached an equilibrium (a "static state"). As such, determination of the output is time-independent as the calculated output concentrations reflect the ultimate concentrations of these output molecules after the reactions have reached an equilibrium.

In another embodiment, the present disclosure provides methods, systems and program codes for determining the time point ("maximum reaction time") at which all biochemical reactions in a biochemical reaction network reach an equilibrium. The methods, for instance, can entail generating a number of matrices at a number of different time points, and then comparing the concentrations of the output molecules at these time points to determine when an equilibrium is reached.

In yet another embodiment, the maximum reaction time can be determined for a biochemical reaction network for a variety of concentrations of the input molecules. It is noted that larger ranges of input concentrations may require longer reaction times to reach an equilibrium, and that the reaction times for increase vs. decrease of an input concentration may differ. Therefore, to ensure that a static state is reached for all biochemical reactions in a network for any given concentration of an input molecule, a maximum reaction time can be calculated using reasonably large ranges of input molecule concentrations, and measuring reaction times for both increase and decrease of input concentration It is contemplated that for determining a static state, the reactions do not have to reach an absolute equilibrium, and it is allowed so long as the concentrations of the output molecules do not increase or decrease substantially within a time period. Accordingly, a predetermined "threshold" value can be used when determining whether a biochemical reaction has reached an equilibrium. For instance, when the change of an output molecule's concentration, between two time points, does not exceed a corresponding threshold, it can be said that the reaction has reached its static state.

As such, a dynamical simulation can be created with input-output functions and the maximal reaction time. Applying one or more input concentrations for time periods including at least the maximum reaction time, and doing this repeatedly with different concentrations, allows to generate a dynamical model. Such a dynamical simulation can be achieved with just lookup of the output values for the input concentrations, and applying the output values for the duration of the inputs. In this way a representation of concentration changes over time is generated in a fast and efficient way from the pre-computed matrix. This allows the simulation method to be applied to large (>200 molecule species) and very large (>1000 molecule species) models, which are beyond other embodiments of mass-action kinetic models for reasons of computational efficiency and techniques for interpreting and analyzing these models.

Generation of a Look Up Matrix for Determining the Output of a Biochemical Reaction Network Accordingly, one embodiment of the present disclosure provides methods, computing devices and program code embedded in a non-transitory computer-readable medium, for the determination of the output of a biochemical reaction network. For instance, in one embodiment, a method is provided for determining the concentration of each of one or more output molecules of biochemical reaction network comprising two, or three or more biochemical reactions and one or more input molecules. In some aspects, the method comprises generating, by a computer, a look up matrix between the one or more output molecules and the one or more input molecules, wherein the matrix comprises a calculated concentration for each of the output molecules produced by the biochemical reaction network, at a time point, from each of the one or more input molecules at each of one or more concentrations for each of the one or more input molecules, such that the concentration of each of the one or more output molecules can be determined at a given concentration for each of the one or more input molecules by looking up the matrix. In some aspects, the biochemical reaction network comprises four, or five, or six, or seven, or eight, or nine, or 10, or 15, or 20 or 25 or more biochemical reactions.

Once the look up matrix is generated, the concentration of each of the one or more output molecules can be determined, at a given concentration for each of the one or more input molecules by looking up the matrix.

In one aspect of the method, device or medium, the set of the three or more biochemical reactions is reversible. In this respect, the mass of substances in the system is conserved and any species is both produced and degraded. A "reversible" reaction set, as used here, refers to a set of biochemical reactions such that the total mass of all biochemical compounds is retained in the system, and all species are both produced and degraded by at least one reaction. This can be obtained by using reactions that are either reversible themselves (e.g., complex formation) or by chains of reactions such that the substrate of a reaction is also the product of another reaction (e.g., enzymatic reactions) in the system.

"Input molecules" and "output molecules" as used herein, refer to any molecule in a biochemical reaction. In this context, an input molecule is one that will have a given concentration during a particular modeling, and does not have to be a reactant or substrate (or more generally a molecule on the left hand side of a reaction) in a reaction. Likewise, an output molecule is one who concentration is to be predicted in the modeling, and does not have to be a product (or more generally a molecule on the right hand side of a reaction) in a reaction.

The look up matrix includes concentrations of the output molecules produced by the biochemical reaction network, calculated with concentrations of the input molecules, at one or more time points. Any method known in the art for calculating the output of a biochemical reaction based on input amounts can be used for such calculation. For instant, one commonly used method entails solving a set of differential equations which represents the set of biochemical reactions.

The look up matrix can be generated at a single time point or multiple time points. In one aspect, the single time point or at least one of the multiple time points is at or after a reaction time (or "delay time") required for one or more biochemical reactions in the biochemical reaction network to substantially reach an equilibrium. In a particular aspect, the single time point or at least one of the multiple time points is at or after a reaction time required for all biochemical reactions in the biochemical reaction network to substantially reach an equilibrium.

For a single reaction, the reaction time required to substantially reach an equilibrium can be termed the "equilibrium-reaching reaction time". For an entire biochemical reaction network, the reaction time required for all of the involved biochemical reactions to substantially reach an equilibrium can be referred to as the "maximum equilibrium-reaching reaction time," or simply "maximum reaction time."

"Substantially reaching an equilibrium," as used herein, refers to a biochemical reaction being at a state where the change (increase or decrease) rate of any of the input or output molecules is less than about 10%, or alternatively less than about 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.02%, 0.01 or 0.001 over a time period of 100 seconds, or shorter, or longer, as fits the application and use of the model.

Fitting of the Look Up Matrix

Once the look up matrix is generated, the matrix can be used to generate look up curves by fitting entries in the matrix. As the matrix only includes, a finite number of entries for each input and each output for each reaction, a fitted function (look up curve) can provide additional value for predicting output concentrations from input concentrations, or combination of such concentrations, not found in the matrix.

In one aspect, each of the biochemical reactions is fitted alone. In another aspect, some or all of the reactions in the network are fitted together. Fitting a finite number of data points to form a curve or equation is sometime referred to as "curve fitting." Various methods for curve fitting are known in the art and the skilled artisan would readily identify those suitable for the current purpose.

In one embodiment, the fitting is carried out with a saturating hyperbolic function. A "saturating hyperbolic function," as used herein, refers to a function that is defined as $$y = f(x) = y_{max} - \frac{y_{max} - y_{min}}{1 + \left(\frac{x}{C}\right)^n}$$

or $$y = f(x) = y_{min} - \frac{y_{min} - y_{max}}{1 + \left(\frac{x}{C}\right)^n},$$

such that the parameters $y_{min}$, $y_{max}$, C and n are determined by the curve fitting (where $y_{min}$ is often 0).

Other known methods for curve fitting include polynomial interpolation, ordinary least squares, and total least squares, without limitation.

Once the look up curves or functions are determined, the curves or functions alone, without the look up matrix, can be used to achieve the same goal as the matrix does, e.g., predicting the concentrations of output molecules from concentrations of the input molecules.

Local Tuning

Methods for tuning individual look up curves (or functions) are also provided. In some embodiments, one or more curves may be tuned to be closer to a desired curve, such as one determined experimentally.

For a single reaction, the parameters in the curve can be updated to make the curve match the desired curve. In a more complex biochemical reaction network, however, this is not the end of the inquiry, as typically a reaction interacts, and thus is interconnected, with other reactions ("neighboring reaction"). For instance, the output molecule of one reaction may be the input to another reaction in the network. Adjustments of parameters in the former reaction, therefore, necessarily impact the latter. The changes of these latter reactions, further, may impact still other reactions that are interconnected with these latter reactions.

It is discovered, however, that the impacts of the change of one reaction on other reactions in a network do not "travel" far. That is, only a small number (e.g., 1, 2, 3, 4 or 5) of neighboring reactions undergo substantial changes once one reaction is changed. Accordingly, for a matrix of look up curves, only a small number of curves require updating once the parameters for one of the curves are changed.

In some embodiment, the tuning of a matrix of look up curves in order to fit one of the curves to a target curve entails the steps of:
(a) adjusting the parameters to fit the curve to the target curve;
(b) adjusting the parameters of other curves in the matrix, which correspond to other biochemical reactions in the network, according to the adjustment in step (a);
(c) determining whether the adjustments in step (b) for the corresponding curve are within a desired error range; and
(d) if the adjustments are not within the desired error range, repeat steps (a)-(c) until the adjustments are within the desired error range.

Error ranges can be pre-determined using historical data, or decided on the fly. For instance, in any of the parameter in a curve for a neighboring reaction is changed more than a certain percentage (e.g., 5%, 10%, 25% or 50%) of the absolute value of the parameter, such change would be considered to be beyond a desired error range. In some embodiments, it is contemplated that for a complex biochemical reaction network that includes more than 20, 50, 100, 200 or more reactions, only a small number (e.g., fewer than 10, 5, 4, 3 or 2) reactions need to be updated once one of the reactions is changed.

This tuning method is particular useful for optimizing a look up matrix with respect to reactions that are important to modeling or are suspected to be inaccurate. With such information in mind, one can then design a computational modeling experiment or a web lab experiment to obtain a real-world target curve for the reaction, and then use the disclosed method of calibrate/fit the curve in the matrix to the target curve effectively. The experimental example provided below, in FIG. 3A-B, is an illustration for this method.

Calculation of Time Required to Reach Equilibria for all Reactions

The look up matrix of the present disclosure can be used to determine the equilibrium-reaching reaction time or maximum reaction time for biochemical reactions or networks.

To achieve this, in one embodiment, a look up matrix is generated at each of a range of candidate time points, or is generated to include data at each of a range of candidate time points. In one aspect, these time points include one or more that are estimated to be lower than, and one or more that are estimated to be longer than, the equilibrium-reaching reaction time or the maximum reaction time. Then, the equilibrium-reaching reaction time or the maximum reaction time can be determined by examining the matrix or matrices.

Accordingly, in one embodiment, provided is a computer-implemented method for determining the reaction time required for a biochemical reaction network to substantially reach an equilibrium, wherein the biochemical reaction network comprises three or more biochemical reactions and three or more input molecules, the method comprising, (a) generating, by a computer, a look up matrix between the one or more output molecules and the three or more input molecules, wherein the matrix comprises a calculated concentration for each of the output molecules produced by the biochemical reaction network, at a time point, from each of the three or more input molecules at a concentration of each of the three or more input molecules, and (b) repeat (a) for a plurality of time points, at least one of the time points of the plurality being likely longer than an estimated maximum reaction time, (c) comparing calculated concentrations for each of the output molecules at the plurality of time points to determine the maximum reaction time.

Modeling for Dose Response

The look up matrix of the present disclosure can also be used to model dose response.

To this end, a look up matrix can be generated with data points collected or predicted from a plurality of dose points of a test agent or test agents ("inputs") and measured substances ("outputs") in the experimental system. Optionally, the matrix or matrices is fitted to provide one or more look up curves or functions. Therefore, the look up matrix or look up curve provides a bona fide dose response curve or function for arbitrary pairs of species in the complex model, assuming steady-state conditions have been reached. This means that the modeling technique allows to infer a dose-response curve for substances which are linked by an arbitrary number of reactions in the model.

Assessment of Disease States and Therapeutic Targets

The look up matrix of the present disclosure can also be used to assess disease states and effects of pharmaceutical agents.

Disease states are often characterized by altered concentrations of molecules within a biochemical reaction network compared to the healthy state. In particular, disease-related concentration changes can result in an altered system state and induce compensatory new signaling interactions. Pharmacological intervention in many cases aims to establish drug targets to normalize or restore the system state. The current method can be used to analyze the effect of altered molecule concentrations in a transparent and mathematically simple way, by comparing matrices of input-output reactions. In particular, the extent of the spread of a local pharmacological intervention in the biochemical reaction network will be much easier to predict by applying the concept of dose-dependent modularity. Accordingly, the effect of such a pharmacological intervention can be assessed. In this respect, positive effects towards normalization of the system state suggest such intervention as a valid potential pharmaceutical target. Applying this method also means that even large data sets, e.g., on patient variability, can be analyzed and significant inferences on function be made, which is difficult with other methods.

Computer Network and Access to Information

It will be appreciated by the knowledgeable reader that systems and methods of the present disclosure can be implemented on any computer devices and computer networks.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the present invention have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present invention may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, mini-computers, mainframe computers, and so on. Embodiments of the invention may also be practiced in distributed and cloud computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

It should be noted that although the discussions herein may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention. Such variations will depend on the software and hardware systems chosen and on designer choice. It is understood that all such variations are within the scope of the invention. Likewise, software and web implementations of the present invention could be accomplished with standard programming techniques with rule based logic and other logic to accomplish the various database searching steps, correlation steps, comparison steps and decision steps.

EXPERIMENTAL EXAMPLES

The following examples are provided to illustrate certain aspects of the present disclosure and to aid those of skill in the art in practicing the disclosure. These examples are in no way to be considered to limit the scope of the disclosure. Various scientific articles are cited by reference numbers and the full citations are included at the end of specification.

Example 1

This example demonstrates that a look up matrix generated as described in the present disclosure can be used to effectively determine, accurately, the output of a biochemical network with greatly reduced computational burden. More details of this example can be found in Scheler "Transfer Functions for Protein Signal Transduction: Application to a Model of Striatal Neural Plasticity," PLoS ONE 8(2):e55762, 13 pages. doi:10.1371/journal.pone.0055762 (2013).

This example presents a new formulation for biochemical reaction networks in the context of protein signal transduction. The model consists of input-output transfer functions. Collectively, these transfer functions constitute an example look up matrix of the disclosure. These transfer functions are derived from differential equations, using stable equilibria.

This example selects a set of 'source' species, which are interpreted as input signals. Signals are transmitted to all other species in the system (the 'target' species) with a specific delay and with a specific transmission strength. The delay is computed as the maximal reaction time until a stable equilibrium for the target species is reached, in the context of all other reactions in the system. The transmission strength is the concentration change of the target species. The computed input-output transfer functions can be stored in a matrix, fitted with parameters, and even recalled to build dynamical models on the basis of state changes.

By separating the temporal and the magnitudinal domain this example can greatly simplify the computational model, circumventing typical problems of complex dynamical systems. The transfer function transformation of biochemical reaction systems can be applied to mass-action kinetic models of signal transduction. The example shows that this approach yields significant new insights while remaining a fully testable and executable dynamical model for signal transduction. In particular this method can deconstruct the complex system into local transfer functions between individual species.

As an example, this example examines modularity and signal integration using a published model of striatal neural plasticity. The modularizations that emerge correspond to a known biological distinction between calcium-dependent and cAMP-dependent pathways. Remarkably, this example found that overall interconnectedness depends on the magnitude of inputs, with higher connectivity at low input concentrations and significant modularization at moderate to high input concentrations. This general result, which directly follows from the properties of individual transfer functions, contradicts notions of ubiquitous complexity by showing input-dependent signal transmission inactivation.

Biochemical reaction systems are usually conceptualized as dynamical systems—systems that evolve in continuous time and may or may not receive additional input to the system. Mathematically, this can be expressed by sets of ordinary differential equations (ODE), such that rates of concentration changes correspond to mass-action kinetic parameters. This example uses existing mass-action dynamical systems to propose an alternate or additional framework for modeling and interpretation of biochemical reaction systems. This example provides an algebraic analysis of biochemical reaction systems as a matrix of concentrations for all species, given certain input concentrations. These concentrations correspond to steady-state amounts which are reached after a delay time, and the delay times can be measured by the system as well.

This example uses an arbitrary published model (Lindskog et al., PLoS computational biology, 2(9):e119, September 2006) as an example for a ODE dynamical model of biochemical reactions. The model simulates intracellular signal transduction from receptor binding to molecular targets in different cellular compartments, as an important component in the long-term regulation of protein expression implied in neural and synaptic plasticity. In striatal neurons, both a calcium-dependent pathway and a cAMP-dependent pathway are activated during the initiation of neural plasticity by NMDA/AMPA receptors and neuromodulator receptors such as dopamine D1 receptors. Their effects and the integration of signaling on common targets such as kinases and phosphatases have been the subject of a number of computational models. In particular, the role of the DARPP-32 protein in striatal neurons in determining the outcome of membrane signaling has been modeled by different groups, based on a common set of experimental data. Many similar models have been developed in the last 10-12 years in different areas of biology. Models with dozens or more of species have up to a 100 or more equations and are consequently complex and difficult to understand as continuous dynamical systems. A transformation into a matrix-based formulation of input-output functions, even at the cost of a loss of fast dynamical modeling, promises considerable gain of insight and access to a different set of mathematical tools. Simple mass-action kinetic models may be criticized for disregarding the real complexity of spatio-temporal molecular interactions. Some alternatives use spatial grids and stochastic versions of biochemical reactions to capture this complexity. However, certain variations, such as compartmental modeling with diffusion, altered kinetics for anchored proteins, or employing molecular kinetics as the basis for binding constants may be employed within the mass-action kinetic framework to achieve better correspondence with the biological reality. These variations can be directly transferred to the proposed model as well.

In the current approach, this example identifies input nodes, and then pre-compute the outcomes for all internal species (target species) in response to biological meaningful ranges and combinations of inputs. This allows to analyze a biochemical reaction system under all possible input conditions. The analysis can be done for arbitrary ODE models, provided minimal requirements on conservation properties are realized. The results are stored as vectors or matrices ('systemic protein signaling functions' (PSFs)) and can be fitted with functional parameters. It is an important aspect of the model that computations are done systemically. In section "Elementary Biochemical Reactions", source-target interactions are first analyzed in isolation ('elementary PSFs'). They all constitute hyperbolic saturation functions, therefore rate parameters can be uniformly translated into functional parameters for signal transmission strength. But in a systemic context, source-target interactions change because of additional influences on the species from other equations in the system (section "Systemic PSF Analysis"). Therefore a fitted systemic PSF from A to B is different from the elementary PSF. The pre-computed, systemic PSFs may be used to create state-change simulation models, i.e., discrete-time models, which can be compared with continuous ODE models (section "Systemic Delay and State-change Dynamics"). What is significant and new about this method is that this method can extract systemic transfer functions from the complex system, and thereby dissect the system into parts. This method can analyze the transmission properties of individual species, compare their minimum and maximum values, and the functional shape of their transmission strength. Specifically, this example shows under which circumstances a link is functional, i.e., actually transmits information (section "Computing Input-dependent Modularity").

The analysis has a number of restrictions. An important restriction is that the present model does not allow for analysis of fast interactions below the resolution of settling into steady-state. The requirement of conservation of mass guarantees that for each input concentrations will eventually settle to some equilibrium value, but due to the prevalence of feedback interactions, they may still produce transients or dampened oscillations. This means that fast fluctuations of input will not be adequately simulated using pre-computed PSF functions alone. It is then necessary to refer to the underlying ODE model. The model is most suitable for studying disease states, pharmacological interventions, genetic manipulations, miRNA interference, or any system conditions which fundamentally alter the presence or concentration of molecular species. These conditions may then be tested either in steady-state or with a sequence of sufficiently slow input constellations. A second restriction is that the model inherits parameter uncertainty from mass-action kinetic models. These parameters are derived from experimental measurements, but typically with a high degree of uncertainty. The present method, however, offers a clear distinction between elementary and systemic functional parameters and explains why experimental measurements are so highly dependent on the systemic context. This example has treated elementary parameters as given by the underlying model (Lindskog et al., 2006). In principle, systemic functional interactions can be measured experimentally, and in the model each interaction can be adjusted separately. This may offer a new theoretical approach towards finding adequate elementary rate parameters.

Materials and Methods
System Definition

A biochemical reaction system formulation for signal transduction contains two different types of reactions:

1. Complex Formation

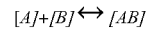

2. Enzymatic Reactions

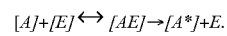

The system has concentrations for species A, B and E (A*, AE and AB can be calculated), a set of kinetic rate parameters $k_{on}$ and $k_{off}$ for the forward and backward binding reactions in complex formation, and $k_{cat}$ for the rate of enzymatic production. The equational structure, the kinetic parameters and the initial concentrations of the model (Lindskog et al., 2006) are reproduced in Tables 1, 2, 3, and 4, with slight modifications: Equation 40 was added to 'close the loop' from AMP to ATP and thus provide for conservation of all molecules in the system. Conservation of mass is necessary in order for all species to reach equilibrium. It means that for any forward reaction there needs to be a reverse reaction, such that any species receives both input and output ('weakly reversible system'). This implies that pure loss reactions, like endocytosis or diffusion across the cell membrane (secretion) cannot adequately be modeled with this system, unless balancing reactions are added which make up for the loss. For instance, for endocytosis of a ligand-bound receptor, both the ligand and the receptor, possibly independently, have to be recycled, which means that bridging equations for receptor-ligand dissolution in the endocytosed state, and input rates for receptors and ligands have to be added. Secondly, the species PP1 and its interactions (4 equations) were left out, since they contain a complex which dissolves into its 3 components in one step: this would require a, fairly trivial, addition to the current PSF system implementation. The system can be depicted as a bipartite graph with nodes for species and nodes for reactions.

TABLE 1

Reactions in the cAMP pathway

| | | $k_{on}$ | $k_{off}$ | $k_{cat}$ |
|---|---|---|---|---|
| 1 | Da + D1R ↔ DaD1R | 0.00111 | 10 | |
| 2 | DaD1R + Gabc ↔ DaD1RGabc | 0.0006 | 0.001 | |
| 3 | Gabc + D1R ↔ GabcD1R | 6e−005 | 0.0003 | |
| 4 | GabcD1R + Da ↔ DaD1RGabc | 0.00333 | 10 | |
| 5 | DaD1RGabc → DaD1R + GoaGTP + Gbc | | | 20 |
| 6 | GoaGTP → GoaGDP | | | 10 |
| 7 | GoaGDP + Gbc → Gabc | 100 | | |
| 8 | GoaGTP + AC5 ↔ AC5GoaGTP | 0.0385 | 50 | |
| 9 | ATP + AC5GoaGTP ↔ AC5GoaGTP_ATP → cAMP + AC5GoaGTP | 0.000128 | 0.261 | 28.46 |
| 10 | AC5 + Ca ↔ AC5Ca | 0.001 | 0.9 | |
| 11 | AC5Ca + GoaGTP ↔ AC5CaGoaGTP | 0.0192 | 25 | |
| 12 | ATP + AC5CaGoaGTP ↔ AC5CaGoaGTP_ATP → cAMP + AC5CaGoaGTP | 6e−005 | 0.131 | 14.23 |
| 13 | PDE1 + Ca4CaM ↔ PDE1CaM | 0.1 | 1 | |
| 14 | cAMP + PDE1CaM ↔ PDE1CaM_cAmp → AMP + PDE1CaM | 0.0046 | 44 | 11 |
| 15 | cAMP + PDE4 ↔ PDE4_cAMP → AMP + PDE4 | 0.02 | 72 | 18 |
| 16 | PKA + cAMP ↔ PKAcAMP2 | 2.6e−005 | 0.006 | |
| 17 | PKAcAMP2 + cAMP ↔ PKAcAMP4 | 3.46e−005 | 0.00 | |
| 18 | PKAr + PKAc ↔ PKAcAMP4 | 0.00102 | 0.0048 | |

TABLE 2

Reactions in the Ca pathway

| | | $k_{on}$ | $k_{off}$ | $k_{cat}$ |
|---|---|---|---|---|
| 19 | Ca4CaM + PP2B ↔ PP2BCa4CaM | 1 | 0.3 | |
| 20 | PP2BCa2CaM + Ca ↔ PP2BCa4CaM | 0.1 | 10 | |
| 21 | CaM + PP2B ↔ PP2BCaM | 1 | 3 | |
| 22 | Ca2CaM + PP2B ↔ PP2BCa2CaM | 1 | 0.3 | |
| 23 | PP2BCaM + Ca ↔ PP2BCa2CaM | 0.006 | 0.91 | |
| 24 | CaM + Ca ↔ Ca2CaM | 0.006 | 9.1 | |
| 25 | Ca2CaM + Ca ↔ Ca4CaM | 0.1 | 1000 | |
| 26 | Ca4CaM + CaMKII ↔ CaMKIICa4CaM | 0.00075 | 0.1 | |
| 27 | CaMKIICa4CaM → CaMKIIpCa4CaM | | | 0.005 |
| 28 | CaMKIIpCa4CaM → CaMKIICa4CaM | | | 0.015 |

TABLE 3

DARPP-32 reactions

| | | $k_{on}$ | $k_{off}$ | $k_{cat}$ |
|---|---|---|---|---|
| 29 | DARPP32 + PKAc ↔ DARPP32PKAc → pThr34 + PKAc | 0.0027 | 8 | 2 |
| 30 | PP2A + PKAc ↔ PKAcPP2A → PP2Ap + PKAc | 0.0025 | 0.3 | 0.1 |
| 31 | PP2Ap → PP2A | | | 0.004 |
| 32 | pThr34 + PP2BCa4CaM ↔ pThr34PP2B → DARPP32 + PP2BCa4CaM | 0.001 | 2 | 0.5 |
| 33 | pThr34 + PP2A ↔ pThr34PP2A → DARPP32 + PP2A | 0.0001 | 2 | 0.5 |
| 34 | DARPP32 + Cdk5 ↔ DARPP32Cdk5 → pThr75 + Cdk5 | 0.00045 | 2 | 0.5 |
| 35 | pThr75 + PKAc ↔ pThr75PKc | 0.00037 | 1 | |
| 36 | pThr75 + PP2Ap ↔ pThr75PP2Ap → DARPP32 + PP2Ap | 0.0004 | 12 | 3 |
| 37 | pThr75 + PP2A ↔ pThr75PP2A → DARPP32 + PP2A | 0.0001 | 6.4 | 1.6 |
| 38 | 1PP2A + 4Ca ↔ 1PP2Ac | 7.72e−012 | 0.01 | |
| 39 | pTh75 + PP2Ac ↔ pThr75PP2Ac → DARPP32 + PP2Ac | 0.0004 | 12 | 3 |
| 40 | AMP → ATP | | | 10 |

TABLE 4

Concentrations

| D1R | 500 | CaMKII | 20000 | PDE1 | 4000 | PP1 | 5000 |
|---|---|---|---|---|---|---|---|

TABLE 4-continued

Concentrations

| Gabc | 3000 | DARPP32 | 50000 | PDE4 | 2000 | Cdk5 | 1800 |
|---|---|---|---|---|---|---|---|
| AC5 | 2500 | PP2A | 2000 | PKA | 1200 | Ca | 1000 |
| ATP | 2e+006 | PP2B | 4000 | CaM | 10000 | Da | 5000 |

PSF Analysis

To set up source-target functions, this example selects input nodes from the available species nodes. In this example, Da (dopamine as ligand for the D1 receptor) and Ca (extracellular calcium that diffuses through ion channels in the membrane) are used. This example uses input concentrations over a specified range (e.g., between 60 nM and 5 μM for Da), sample over the range with e.g., n=20 steps, and uses the differential equation implementation of the system to calculate the output values for all species for each sampling step. Because of the conservation of molecules, all species reach steady-state after a sufficient period of time. This example defines steady-state pragmatically by relative change of less than 2% over 100 s. This example also uses the established terminology of $EC_{10}$, $EC_{50}$, $EC_{90}$ etc. to indicate 10, 50 or 90% of steady-state concentration value. Additionally, this example calculates the delay in reaching steady-state. It stores input-target concentration mappings in a vector (single-input system), or a matrix (multiple-input system). This example fits the vectors with hyperbolic or linear functions, using standard techniques in Matlab (fminsearch). In this way this example derives parameters which can be analyzed and used instead of the explicit vectors. In this example, the fitting is only done for single-input systems.

All information on source-target transfer functions for the complete, complex signaling system ('systemic PSF') can be stored in a static data structure. For each species, it contains its concentration range, and for each reaction, it contains the parameters of the functional fit. It gains the possibility to regard any species as source and any other species as target (they may be coupled by an arbitrary number of reactions) and obtain a systemic PSF as the transfer function between them. This representation allows to analyze the complex signaling system by its parts, i.e., as a set of matrices or vectors, which is the main achievement relative to the ODE dynamical system. In addition, dynamical simulation with appropriate update times may be realized by the PSF representation alone, i.e., the PSF simulation is not in itself atemporal, but only discrete and fairly slow.

This example visualizes the data structure as a bipartite graph, and label it with the calculated numeric values. Each species node is labeled with its attainable concentration range given the input range. For complex formation reactions, this examples show both [A]→[AB] and [B]→[AB]. For enzymatic reactions this example shows [E] as the source and [A*] as the target ([E]→[A*]). The result is a labeled bipartite graph, called a 'weighted dynamic graph'.

Results
Elementary Biochemical Reactions

A biochemical reaction is represented by a time-independent signal transfer function, such that y=ƒ(x) for two species x, y. This is achieved by designating a source species x and then calculating the steady-state value for another species, the target species y, for any value of x, given the differential equations for the biochemical reaction. For complex formation $$[A]+[B] \leftrightarrow [AB]$$

where the total concentrations for [A] and [B] and kinetic rate parameters $k_{on}$, $k_{off}$ (with $K_d=k_{off}/k_{on}$) are given, the differential equations are:

$$dxdt(A)=k_{off}[AB]-k_{on}[A][B]$$

$$dxdt(B)=k_{off}[AB]-k_{on}[A][B]$$

$$dxdt(AB)=-k_{off}[AB]+k_{on}[A][B].$$

One may now calculate the concentration values ƒ(x)=y for a target species [AB] given a range of input values for x, e.g., the source species [A] (FIG. 1A).

In this way this example separates the calculation of the signal response magnitude, i.e., the steady-state concentration, from the calculation of the time until a steady-state value is reached, the delay. For different x, ƒ(x) will be reached after a variable delay (FIG. 1B).

With some modification, the same transformation applies to enzymatic reactions. The kinetic rate parameter are $K_d=k_{off}/k_{on}$ (for ↔) and $K_{cat}$ (for →).

$$[A]+[E_1] \leftrightarrow [AE_1] \rightarrow [A^*]+[E_1].$$

Here it is required that the enzymatic reaction is reversible, i.e., a reaction $$[A^*] \rightarrow [A]$$

exists. (For instance, $$[A^*]+[E_2] \leftrightarrow [A^*E_2] \rightarrow [A]+[E_2]$$

is a reaction that reverses [A*].) The differential equations, with $k_{cat2}$ for [A*]→[A], are:

$$dxdt(A)=k_{off}x[AE_1]-k_{on}x[A][E_1]+k_{cat2}[A^*]$$

$$dxdt(E_1)=(k_{off}+k_{cat})[AE_1]-k_{on}[A]^*[E_1]$$

$$dxdt(A^*)=k_{cat}[AE_1]-k_{cat2}[A^*]$$

$$dxdt(AE_1)=k_{on}x[A][E_1]-(k_{off}+k_{cat})[AE_1].$$

Given concentrations for $E_1$, A and kinetic rate parameters $K_d$, $k_{off}$ and $k_{cat}$ for both reactions, a function for x as the source species [E1] and y as the target species [A*] can then be derived (FIG. 1C).

In both cases the curve can be fitted by a saturating hyperbolic function:

$$y = f(x) = y_{max} - \frac{y_{max} - y_{min}}{1+\left(\frac{x}{C}\right)^n}.$$

Here $y_{min}$, the baseline concentration, is usually set to 0.
If one chooses [A] as the target of [E1], one can get a negative slope PSF.

$$y = f(x) = y_{min} - \frac{y_{min} - y_{max}}{1+\left(\frac{x}{C}\right)^n}$$

This function is referred to as the 'elementary protein signaling function' or 'elementary PSF.' This function is somewhat related to a Hill equation. A Hill equation is a function fitted to an experimental measurement to derive a dose-response relationship, comparable to the PSF. The Hill equation allows to calculate a fractional concentration θ for the target (e.g., a receptor-ligand complex) from the source concentration [L], given $K_d$, and fitting a parameter n for the steepness of the curve.

$$\theta = \frac{[L]^n}{Kd+[L]^n}$$

The concentration of the other compound of the complex is not used (assumed large), and the absolute magnitude of the target is not calculated. An equivalent for enzymatic reactions is not defined. The parameter n allows to measure the effect of competing binding reactions (n=1 if none are present), which in the current terminology translates into a systemic PSF with multiple binding partners for a single target compound. Systemic PSFs are a more general concept than Hill equations, but they relate to the same type of data, namely dose-response functions in steady-state.

It is noted that signal transmission strength is uniformly characterized by saturating hyperbolic functions. This means that it is highest for low x and diminishes as x increases (FIG. 1D). For instance, in FIG. 1D, a 100% signal increase leads to 100%, 18% or only 6% increase in the target depending on the source concentration. For enzymatic reactions, absolute concentration changes have different effects for sources and targets of a signaling interaction. Signal transmission strength depends on the absolute concentration of the source, the target concentration is irrelevant. This is an important observation, since protein signaling systems are subject to long-term regulation of concentrations. In the context of disease states or other sources of protein expression up-/down-regulation, independence of transmission strength from target concentration may be an important conservative property.

Signal transmission is strongest if a source species is expressed at a low concentration. It is noted, however, that reaction velocity operates inversely to signal transmission strength: a low source concentration means a slow reaction (FIG. 1B). A functioning signaling system would therefore have to use an intermediate range to maximize signal transmission within time constraints. This analysis opens a new way of analysis for a signaling system: Optimization techniques could find a best source range for both time and signal transmission constraints.

Systemic PSF Analysis

A source-target PSF can be derived for any pair of species in a complex biochemical reaction system. For a complex system, or set of equations, this example defines a set of input nodes, and computes the output values for each possible input configuration. The analysis gives the output concentration range (notwithstanding transients in a dynamic context, s. below) for each species, as well as a (fitted) function, or matrix of input-output correspondences. A biochemical reaction will produce a different PSF, when it is elementary or when it is embedded in a context, where the participants of the elementary reaction also participate in other reactions. This is true for both protein complex formation and enzymatic reactions. This example therefore call source-target functions 'systemic PSFs', when they are derived from the context of a specific signaling system.

A systemic PSF, in this context, is an example of a matrix of fitted look up curves of the present disclosure.

This example shows the concentration ranges and the signal transmission functions for the whole system as a weighted dynamic graph for Da as a single input. This example labels each species node with its concentration range, determines source and target species nodes for each reaction node, and provides fits for the systemic PSF, the transfer function that characterizes each reaction. A number of systemic PSFs can be fitted well with a linear function (y=mx+b), showing that systemic PSFs sometimes consist only of a short section from a full mapping of concentration values. Also, many species have only small concentration ranges, which means they don't have much response to Da input.

It is an obvious advantage of the PSF analysis that one is able to dissect the complex system and extract local properties, such as concentration ranges of individual species, and transfer functions for individual reactions under input stimulation. This allows to critically analyze a model, compare these properties with biological data, and adjust or improve the model in a detailed manner.

In FIG. 2, the concentration ranges for some target species are given. It is noted, for instance, that among DARPP-32 phosphorylation variants, pThr75 is always more abundant that pThr34, by an order of magnitude. This is an example of a high-level property, which could be related to biological data. As another example, it is noticed that the active receptor conformation (Da-D1R) remains below 160 nM even under stimulation with 1 μM Da and more. With a D1R total concentration of 500 nM, one could adjust the ligand binding coefficient to produce more or less active receptors. Finally, the analysis shows a very low maximal PKAc level (12 nM) in spite of a total PKA concentration of 1.2 μM. In the original model (Lindskog et al., 2006), blind parameter adjustment has probably generated a very low level of PKAc in order to achieve high signal transmission for phosphorylation of the target species pThr34, which is experimentally required, but which could be achieved in other ways (e.g., PP2B) as well.

With this analysis, properties of individual species become apparent, and they can be compared to biological data, tested and adjusted on a localized basis. Even more interestingly, one could look for principles of 'rational system design', for instance question the transmission of a seven-fold increase of cAMP in the μM range to a maximal three-fold increase in the 10's of nM for PKAc, and analyze given biological systems from this perspective.

In addition to the concentration ranges, this example also has access to the functional mapping between species in the model. The systemic PSFs, like the elementary PSFs, are stored as vectors, which are matched by functional parameters. The advantage of the PSF analysis is that one can probe a complex system on a single reaction level because the influence of the cellular context is encoded in the systemic PSF. Thus one can compare the elementary PSF with its transformation as a systemic PSF for individual reactions. FIG. 3A shows elementary and systemic PSFs for G-protein activation of AC5 and the calcium-activated complex AC5Ca. It is seen that the systemic PSFs are somewhat deflected, compared to the elementary PSF, which is what this example expects from the parallel activation of AC5Ca and AC5 by the same species. One may specify a desired PSF using only functional parameters, and adjust elementary parameters to match the PSF (FIG. 3B). A local change to the Kd binding coefficient between AC5Ca and GoaGTP allows a change in the systemic function. Since other systemic PSFs may be affected by such a change—this can be detected by re-computing the weighted dynamic graph—more adjustments of elementary rate parameters may be indicated, possibly by an iterative process, as provided above, with respect to tuning a fitted curve in a look up matrix locally.

Sampling for multiple inputs yields a transfer function matrix, which can be analyzed for dependence of the target concentration on each input separately. This can be done by standard matrix analysis such as principal component analysis (PCA). For this example, it shows how species which are poised to integrate signals from two different sources do this under the numeric conditions (FIG. 4). For cAMP production (AC5), it is found that AC5GoaGTP is dependent only on Da (FIG. 4A), AC5Ca is only dependent on Ca (FIG. 4B), while AC5CaGoaGTP is almost not activated at all (FIG. 4C). Even though a link of reactions (Ca-AC5Ca-AC5CaGoaGTP-cAMP) exists, signal integration of Ca and Da on AC5 fails because of the weak transmission from GoaGTP to AC5Ca. Signal integration between Ca and Da occurs for cAMP degradation by calcium-dependent calmodulin regulation of PDE1 PP2A with the two variants (calcium-activated) PP2Ac and (PKAc-activated) PP2Ap is another potential source of signal integration (FIGS. 4D, E, and F). The PSF analysis shows when signal integration occurs (here: Da having influence on PP2Ac), and when this effect is negligible (here: Ca not having influence on PP2Ap). This may now be studied for correspondence with the biological situation. These results emphasize the necessity for numeric analysis of input-dependence, beyond the mere existence of links.

Systemic Delay and State-Change Dynamics

This example attempts to use systemic PSFs with their simple and transparent mathematical structure for dynamical simulations. This allows direct experimental testing and fitting by time series measurements beyond dose-response relationships. In order to do this, this example computes the systemic delays, i.e., the reaction time until a steady state is formed. Then one can build a state-change dynamical model from systemic PSFs alone, using the appropriate delays for the input and the update of a system state.

Systemic delays depend on the absolute size of the signal and also the direction (increase/decrease) of signaling. Delays for species in the example system in response to input are shown in Table 5. For the computation of target concentrations only need a ratio such as $k_{on}/k_{off}=Kd$ (binding coefficient) or $k_{cat}/k_{cat2}$ for forward and backward enzymatic reactions. For the delays, the difference between $k_{on}$ and $k_{off}$ or $k_{cat}$ and $k_{cat2}$ defines reaction times for synthesis and degradation. Therefore, delay computations are fairly complex, but the results are often within a fairly narrow range for each reaction (Table 5). For discrete state-change simulations one may use maximal delays for each species.

TABLE 5

Hyperbolic and Linear Function Match for Input-Target PSFs

| Species | $Y_{max}$ | $Y_{min}$ | C | n | b | m | s |
|---|---|---|---|---|---|---|---|
| DaD1R | 163 | | 1723 | 1.73 | 14 | 0.033 | 0.024 |
| AC5GoaGTP | 41 | | 701 | 0.99 | | | 0.00386 |
| AC5CaGoaGTP | | | | 1.83 | | 0.00064 | 0.000423 |
| PKAc | 10.8 | | 223 | 0.85 | 7 | 0.00090 | 0.00071 |
| PP2Ap | 963 | | 103 | 0.86 | 746 | 0.053 | 0.064 |
| cAMP | 1626 | | 959 | 1.1 | 494 | 0.252 | 0.178 |
| pThr34 | 1115 | | 330 | 0.92 | 655 | 0.108 | 0.074 |
| PP2Ac | 59 | 107 | 718 | 1.42 | 84 | −0.0057 | 0.0035 |
| pThr75 | 8397 | 11472 | 523 | 1.83 | 9601 | −0.316 | 0.2 |

Figure 5A:
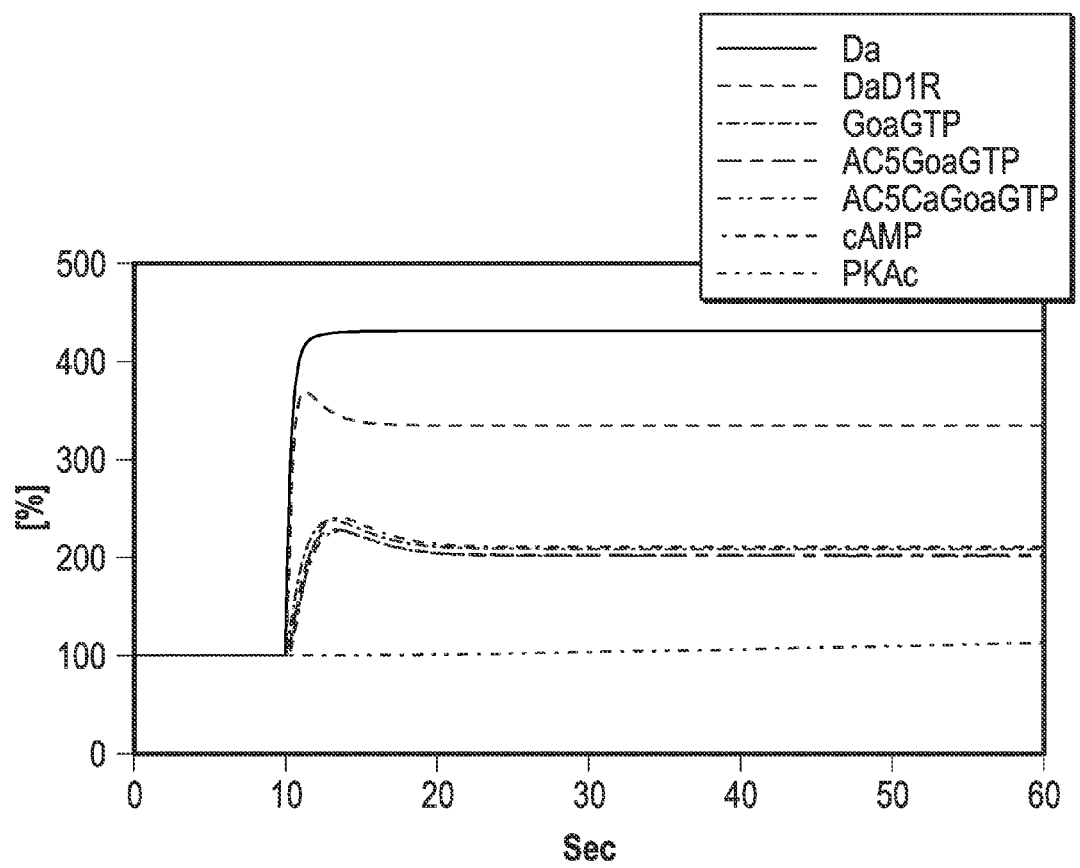
FIG. 5A-D show dynamics of target species to Da input. A. Fast species (<10 s) have transients. The PSF approximation only calculates the steady-state value. B. For slow species no transients are apparent. It may take several minutes to reach steady state. C-D. Dots mark systemic PSF values, thick lines are continuous dynamical simulations by differential equations, thin lines are interpolations between 10 s PSF values. Red arrows mark time points for interpolations for slow species like PP2Ac, PP2Ap, pThr34.
Figure 5B:
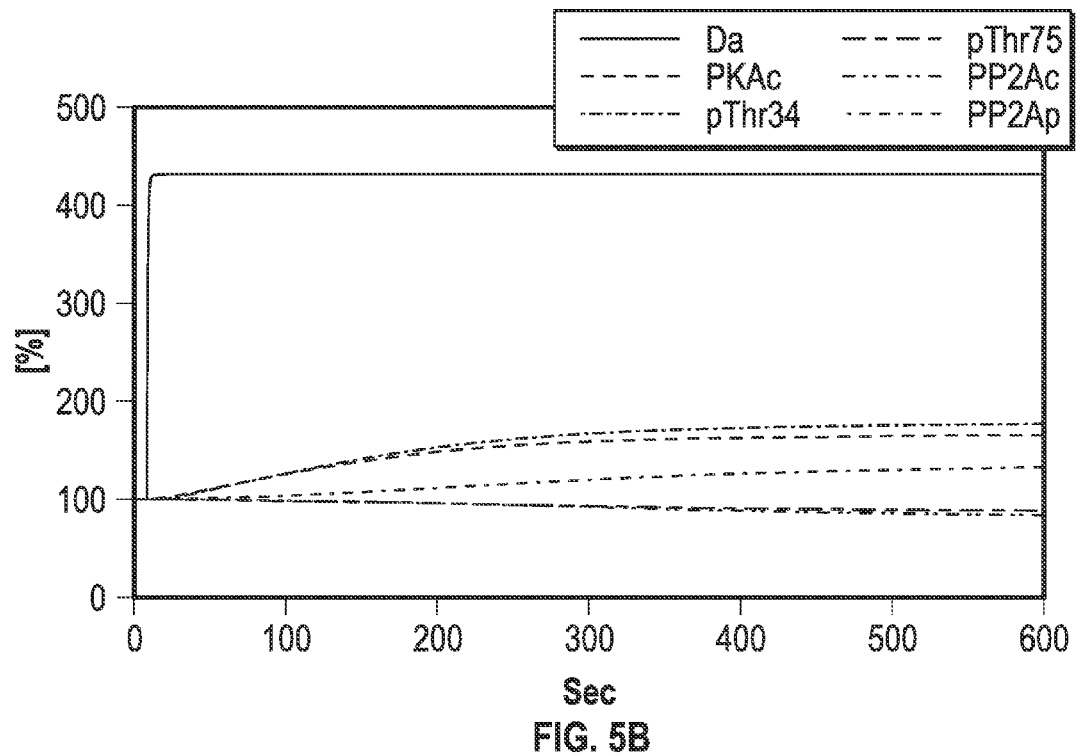

From a biological perspective, this table provides an important test on the validity of the model. In many cases, systemic delays can be measured. For instance, the delay for PKAc at 150-250 s rather than 30-60 s), seems large and may be an indication for a revision of the underlying parameters. From the theoretical perspective, this system seems to operate on separate time scales: 1-10 s, 150-300 s and 450-600 s. Such a separation of reactions by their characteristic delay times is interesting, since it could lead to simulation models with different discrete time scales. Here one may calculate PSF values for fast species with 10 s time resolution, for intermediate species with 300 s time resolution, and for slow species with 600 s time resolution, i.e., system update time for state changes (FIG. 5A-B). It is an empirical question, whether separate time scales rather than a continuum of delay values will prove to be an organizing principle in protein signaling systems. A general study, for instance, using models from the BioModels Database, might give answers to this question. Time scale separation may provide a conservative property of a signaling system against fluctuations of concentrations. If total concentrations in the system change, e.g., by protein expression up- or down-regulation, miRNA interaction, or diffusional processes across compartments, the relevant interactions will continue within each time slice. Concerted regulation of protein expression levels may set a clock for the rapidity of signal transduction.

Systemic dynamics, in contrast to elementary reaction dynamics, need not follow a hyperbolic curve. If there are feedbacks in the system, the dynamics may contain transients, i.e., the concentration may be higher or lower before it settles into its steady-state value. The dynamic response of target species to input are shown in FIG. 5A-B. For a species without a transient response, the actual value of a species at a shorter delay is always bounded by the steady-state value, and all possible concentrations in a continuous-time dynamical system are bounded by the PSF concentration range. However, if there are transients, a PSF-based dynamical simulation will miss these transients and plot a simplified trajectory. This means that results from a PSF analysis with slow inputs cannot be extrapolated to much faster input dynamics—in contrast to continuous-timed dynamical systems where arbitrary time units can be chosen. This restriction may capture a biological reality: steady-state behavior provides the framework and may operate according to rules and principles which are separate from the effects of short term fluctuations.

Figure 5C:
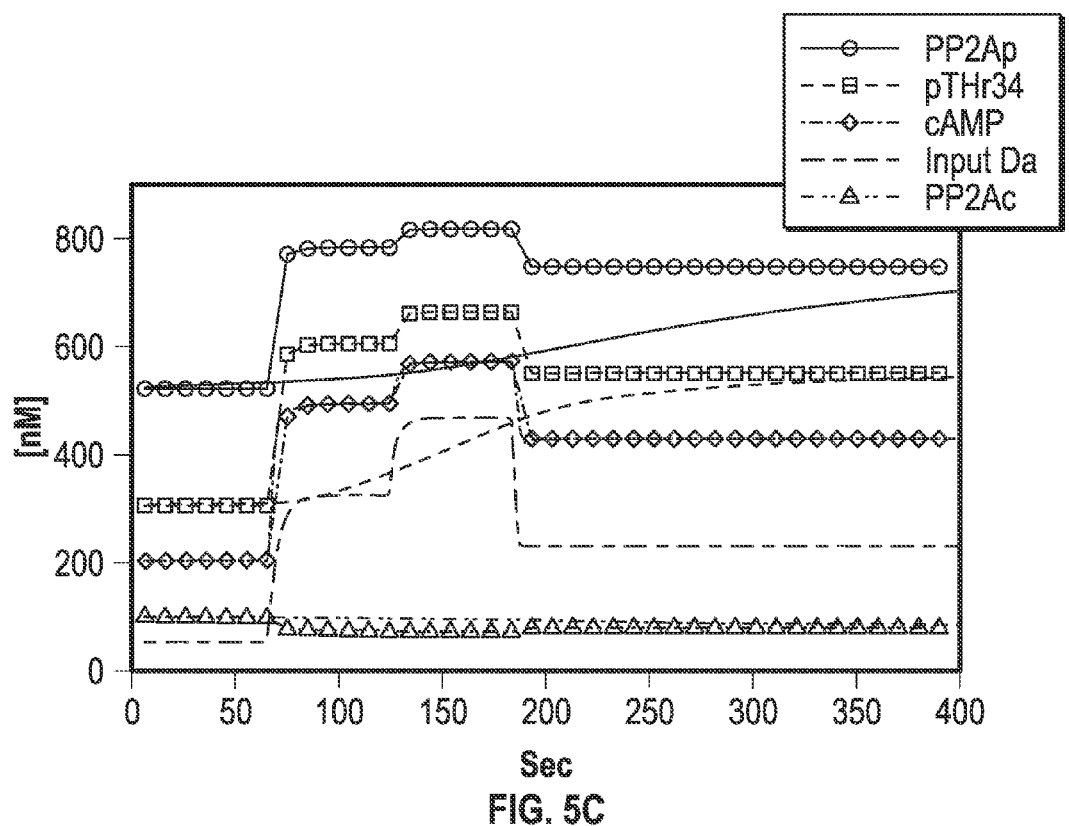
Figure 5D:
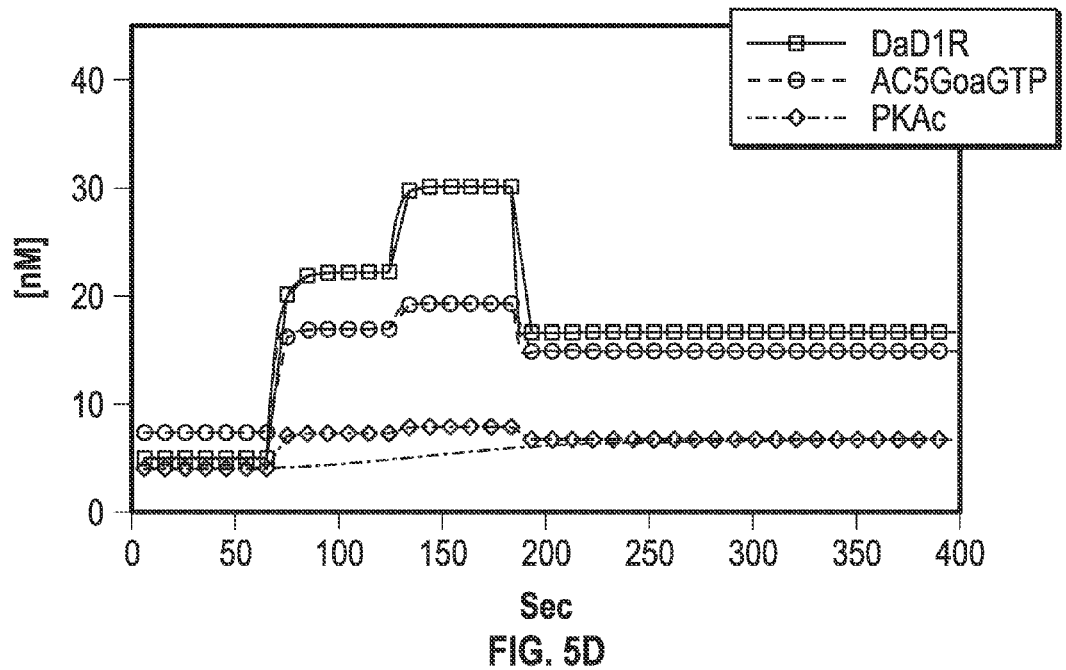

The PSF system allows to generate a dynamical system as a sequence of states defined by fluctuations of input. FIG. 5C-D show an overlay of a differential equation simulation and PSF state change simulation for a sequence of inputs with 10 s duration. Accordingly, the PSF approximation is excellent for all species with a delay time of <10 s. If one plots PSF values for slow species at intervals corresponding to their maximal delays, one may linearly interpolate between points, and in this case achieve a good approximation of the continuous-time model.

A PSF-based dynamical system is an important tool in order to generate a time-series simulation from a calculated model system for comparison with experimental data. The PSF system utilizes parameters which are uniform and have linear error ranges (cf. FIGS. 1A and C), and therefore should improve interaction of the model with the experimental reality. The PSF model will also allow to predict the optimal stimulation times for different inputs such that responses can be measured in steady-state.

Computing Input-Dependent Modularity

Since this example is able to define signal transmission capacity, one has a tool to investigate modularity of a signaling system. As species saturate or return to basal levels, they act as inactive links, i.e., they are stuck at the same concentration value, and cannot transmit further increases or decreases of inputs. The inventor hypothesizes that this effect is actually important in many protein signaling systems. One may define an inactive connection as a species node which has only limited (e.g., <10%) signal transmission capacity. The interconnectedness of a system is then proportional to the number of inactive connections, and a module is a part of the system with few or no active connections to the rest of the system.

In the following this example discusses the activation/inactivation of links with respect to input increases. For instance, given a certain level of extracellular signaling, what happens if this level is raised and then kept at the higher level for some time, sufficient for the system to settle into a new steady state? Which species nodes will respond to the increase and transmit it to downstream targets, and which species will become saturated and only respond with their saturated value? It is also clear that species which have become saturated (inactive) will not respond to fast extracellular signals anymore. This analysis is therefore useful both for the steady-state context and for understanding fast input fluctuations. There is an input level for each target species, where the species ceases to be responsive to further input increases. If that input level has been reached, the species can be considered to have become an inactive connection, i.e., a node which does not transmit signals. One may define systemic PSFs for 'input-target PSFs' from the input to any target species (FIG. 6). It is noticed how number of steps in the computation of a species concentration relates to a lower cut-off value for signal transmission (e.g., DaD1R, AC5GoaGTP, cAMP vs. PKAc, pThr34, pThr75). In other words, earlier steps in the sequence saturate at a higher input level than later steps. Two parallel targets (pThr34, PP2Ap) of an intermediate step (PKAc) may saturate at very different input levels (~3 μM for pThr34 vs. 1.5 μM for PP2Ap). This mechanism demonstrates the effect of a sequence of saturating functions, and constitutes a general principle in the construction of a signal transduction system.

The model allows to study whether a node responds to a specific input with any change of steady-state. This example shows modularization of the system under various Da and Ca input conditions. With Da input and high Ca, species which are proximal to Da input, the receptor-ligand complex DaD1R, the signaling complex through G proteins and adenylyl cyclase AC5, as well as cAMP, are most responsive to Da over a large range of input. Species in the 'integration zone' between Da and Ca, such as DARPP-32, PP2A cease responding to Da increases at lower levels and become inactive links at higher levels. Species in the system with no significant change in concentration at any input level are for the most part proximal to Ca instead of Da, and thus highlight modularity among pathways. In this case, it is seen that Da inputs are transmitted to distant targets only up to an intermediate range and that there are a significant number of species which do not react to Da at all. Above that range, even though closely coupled targets still respond to the input, the signal increase is not registered beyond cAMP production and synthesis. With Ca low there is widespread responsivity to Da up to 1-2 μM and only a few of the calcium-related species do not respond at all. The Da signal is therefore able to influence the calcium-related pathway, provided calcium is low.

When Ca is the input, the calcium-responsive proteins like calmodulin, CaMKII, calcium-activated PP2B (calcineurin) transmit signals, while the GPCR pathway remains almost completely unresponsive. There is some signal integration with calmodulin-activated PDE1 for cAMP. Other than that, it is seen that PP2Ac and the pThr34 variant of DARPP-32 respond strongest to calcium while PP2Ap and the pThr75 variant of DARPP-32 have less or no responsiveness to calcium. With Da low, again, most of the GPCR-related species do not respond to Ca at all, or cease responding at 10-25% of maximal Ca (1-4 μM). However Ca-related species like calmodulin, CamkII, PP2B remain responsive. The difference between the high and low Da condition is small. Here the few existing links from Ca to GPCR (such as Ca regulation of AC5) are not strong enough to influence the GPCR pathway significantly in any condition. In this case, it is not just the saturation that matters, the input signal has limited reach in influencing distant species in general.

This example analyzes a biological system with two 'pathways', the cAMP and the calcium pathway, which are cross-linked in a convergence zone of species which are influenced by both pathways. It is remarkable how clearly three different modules appear: the GPCR/cAMP pathway, the Ca pathway, and the signal integration zone.

There is also a general observation to be made about signal transmission in a protein signaling system: Signal integration is strongest when inputs are low. This is a direct consequence of the effect of coupling saturating nodes. It means that there are few saturating species in the system which impose modularity, and signals spread further. Widespread interconnectedness is only possible at low input levels. Because activation curves for biochemical reactions are mostly uniform hyperbolic (saturating), a stronger modularization with many inactive links results from higher input levels. This may also have implications on transient responses. For instance, phosphatase and kinase response often differs with kinases being saturated only at higher input levels. If and where that is the case, one may observe transient responses that only reflect kinase activity, since phosphatases are saturated and do not participate in signaling, they do not add or subtract and in this way obscure the kinase signal. This shows that the steady-state input-response system may work well as the framework wherein fluctuating signaling operates.

Continuous dynamical systems—systems that use change over time as a system primitive—are notoriously difficult to analyze and may not be the best choice of a tool for signal transduction systems of moderate or large size. Steady-state matrix computations are simple and fast, scale well to very large sizes, and offer multiple opportunities for analysis. By calculating transfer functions from a systemic dynamical model, one can also gain the opportunity to extract and analyze parts of the system. This may help in creating re-usable system parts. This example demonstrated a transformation of a mass-action kinetic biochemical reaction model implemented by a set of differential equations into an input-response transfer function model. The transformation is done by calculating steady-state concentrations for each species in response to a range of input values, and then analyzing the resulting vectors (matrices) as the basis of a transfer function ('PSF'). For small, toy-like networks of few components, such dose-response relationships have been investigated previously. They analyse kinetic models in the same way, however, they don't make a distinction between parameters in elementary interactions, and the actual parameters in a systemic context. They also do not address the question of temporal embedding of the dose-response relations. In the current approach, this example uses dose-response functions, similar to Hill functions, but this example extends the concept. By using rectangular signals, i.e., constant signaling levels, this example calculates the response as the steady-state value.

In addition, this example calculates the time to steady-state from the underlying dynamical model. Only because of this additional computation can one attempt to create a discrete dynamical model—something that is not within the purview of a Hill equation model. Hill equations attempt to fit or create systemic parameters, which are different from elementary parameters, i.e. they do recognize the dependence of the transfer function on the systemic context. The PSF model is an approach of making Hill equations (dose-response relations) work in large-scale modeling.

There are numerous attempts to simplify dynamical models in the temporal domain by creating hybrid models). Sometimes slow interactions are regarded as constant, and only fast interactions are dynamically modeled. Sometimes, fast interactions are replaced by time-independent values and only slow interactions are dynamically modeled. There are also attempts to replace an ODE model by a delay-differential equation (DDE) model, that is, to compute and use explicit time delays and eliminate many intermediate species, simplifying the size of the model.

In the current approach, time and concentration are regarded as separate, which makes it different from any hybrid approach. The main restriction is the assumption of a constant signaling level over periods of time sufficient to induce steady-state. The approach is therefore best suited to check the limiting conditions of a dynamical model, e.g., in drug development applications, where multiple dose-response relations derived from the model can be cross-checked and used to locally improve the model. However, the simple, atemporal transfer functions can also be applied directly: (a) in experimental settings where signal duration can be controlled, and (b) in physiological settings, when fluctuations occur around different mean values, and it models the step changes for the mean extracellular signaling level, but not the short-term fluctuations. It could be shown that PSFs are sufficient to create discrete time dynamical models, with certain restrictions on fast dynamical inputs below the time resolution of the system. The primary focus of the analysis was on single-input systems, where signaling functions can be matched by parameterized hyperbolic functions.

This example showed how the analysis can be extended to multiple-input systems by computing and analyzing PSF transfer matrices. The PSF functions allow to cut through the complexity of the model and examine interactions in a localized way. If continuous dynamical models are being used with the goal of adequately simulating cellular processes, this kind of analysis is an indispensable tool to check for the consequences of the modeling assumptions in terms of dose-response relationships. The analytical tools of the PSF approach may also be used to systematically investigate the effect of localized changes to the system, and to offer local corrections to the complex system in a transparent way.

The extraction of input-target PSFs with characteristic hyperbolic saturating properties allows to determine input level dependent inactivation of a species node. Accordingly, one can define the limits of signal transmission by the distribution of inactive nodes. In the example system, a strong distinction of calcium- and cAMP-dependent pathways and a signal integration zone were revealed. One could see that at low levels of input, widespread interactions are possible, while at higher levels of input, many species enter into a state of a constant function value and become inactive links. This corresponds to biological results and expectations, and provides a foundation for the concept of pathways in signal transduction. For transient responses, the steady-state input-response system provides the boundary values to which the system eventually settles. This is especially interesting if one has saturating response levels, which are unresponsive to further signaling (e.g. phosphatases), and allow transient signals (e.g. kinases) to emerge.

Signal transduction may also be analyzed from the perspective of rational system design. Such work is still in its infancy. One may for instance investigate the effect of negative feedback links on concentration ranges and times to steady state. Another question would be the optimization of a signal transduction system for the trade-off between speed and efficacy of signal transmission. With this choice of model, many new questions can be raised, and old problems like parameter dependency, modularity or signal integration can be addressed in a novel way.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for determining the concentrations of one or more output molecules of a biochemical reaction network, which network comprises three or more biochemical reactions that take one or more input molecules as input and the output molecules as output, the method comprising:
    generating, by a computer, a look up matrix between the output molecules and the input molecules, wherein the matrix comprises a concentration for each of the output molecules produced by the biochemical reaction network from each of the input molecules, at each of one or more concentrations for each of the input molecules,
    fitting the look up matrix to obtain one or more look up curves,
    receiving an inquiry comprising an inquiry concentration for each of the input molecules, and
    determining the concentrations of the output molecules using the look up curves that take the inquiry concentrations as input.

2. The method of claim 1, wherein the fitting comprises fitting each input molecule-output molecule relation in the look up matrix with a saturating hyperbolic function.

3. The method of claim 1, wherein the concentrations for each of the input molecules used to generate the look up matrix are taken at after a reaction time required for the biochemical reaction network to have substantially reached an equilibrium.

4. The method of claim 3, further comprising determining the reaction time.

5. The method of claim 1, wherein the three or more biochemical reactions are reversible.

6. The method of claim 1, further comprising tuning parameters of one of the look up curves that correspond to one of the biochemical reactions against a target curve, wherein the tuning comprises:
   (a) adjusting the parameters to fit the curve to the target curve;
   (b) adjusting the parameters of the curves corresponding to other biochemical reactions that relate to the biochemical reaction according to the adjustment in step (a);
   (c) determining whether the adjustments in step (b) are within a desired error range; and
   (d) if the adjustments are not within the desired error range, repeat steps (a)-(c).

7. The method of claim 6, further comprising obtaining the target curve in an in vivo or in vitro system that comprises the biochemical reaction network.

8. A method for determining the concentrations of one or more output molecules of a biochemical reaction network, which network comprises three or more biochemical reactions that take one or more input molecules as input and the output molecules as output, the method comprising:
   generating, by a computer, a look up matrix between the output molecules and the input molecules, wherein the matrix comprises a concentration for each of the output molecules produced by the biochemical reaction network from each of the input molecules, at each of one or more concentrations for each of the input molecules, and
   determining the concentrations of the output molecules by looking up the matrix with inquiry concentrations of the input molecules.

9. The method of claim 8, wherein the three or more biochemical reactions are reversible.

10. The method of claim 8, wherein the concentrations of the input and output molecules comprises experimental data or computationally modeled data.

11. A computer-implemented method for determining the reaction time required for a biochemical reaction network to have substantially reached an equilibrium, wherein the biochemical reaction network comprises three or more biochemical reactions that take one or more input molecules as input and one or more output molecules as output, the method comprising,
   (a) generating, by a computer, a look up matrix between the output molecules and the input molecules, wherein the matrix comprises a concentration for each of the output molecules produced by the biochemical reaction network from each of the input molecules, at each of one or more concentrations for each of the input molecules for a time point, and
   (b) repeat step (a) for a plurality of time points, at least one of the time points of the plurality being likely longer than an estimated maximum reaction time,
   (c) comparing the concentrations for each of the output molecules at the plurality of time points to determine the reaction time required for the biochemical reaction network to have substantially reached an equilibrium.

12. The method of claim 11, wherein the comparison comprises comparing the difference of concentrations of an output molecule at two time points to a predetermined threshold of concentration change that identifies that an equilibrium is reached.

* * * * *